United States Patent [19]
Chen et al.

[11] Patent Number: 5,843,737
[45] Date of Patent: Dec. 1, 1998

[54] CANCER ASSOCIATED GENE PROTEIN EXPRESSED THEREFROM AND USES THEREOF

[76] Inventors: Lan Bo Chen, 184 E. Emerson Rd., Lexington, Mass. 02173; Shideng Bao, 1699 Cambridge St. #32, Cambridge, Mass. 02138

[21] Appl. No.: 366,547

[22] Filed: Dec. 30, 1994

(Under 37 CFR 1.47)

[51] Int. Cl.[6] ........................... C12N 15/00; C12N 15/85; C27H 71/02
[52] U.S. Cl. ........................... 435/172.3; 435/6; 435/183; 435/320.1; 435/325; 536/23.1; 536/23.2; 536/23.5
[58] Field of Search .................................. 514/44; 435/6, 435/252.37, 183, 172.3, 320.1, 325; 536/23.1, 24.5

[56] References Cited

U.S. PATENT DOCUMENTS 5,585,479   12/1996   Hoke et al. ............................ 536/24.5

OTHER PUBLICATIONS

Gewirtz et al., Facilitating oligonucleotide delivery: Helping antisense deliver on its promise, Proc. Natl. Acad. Sci., vol. 93, pp. 3161–3163, Apr. 1996.

Orkin et al., Report and recomendations of the panel to assess the NIH investment in research on gene therapy, pp. 1–41, Dec. 7, 1995.

Ngo et al., Computational complexity, protein structure prediction, and the Levinthal paradox, The Protein Folding Problem and Tertiary Structure Prediction, pp. 434–440, 1994.

Pawlak A, et al., EMBL Database entry HS3078 (abstract).

Pawlak A, et al., Genomics vol. 26, pp. 151–158 (1995).

Lemaire L, et al., Life Sci 52(11) pp. 917–926 (1993).

Leroy P, et al., Cell 57 (4), pp.549–559 (1989).

Kerr SM, et al., Mammalian Genome 5(9), pp. 557–565 (1994).

Gee SL, et al., Gene (Amsterdam) 14(2), pp. 171–177 (1994).

*Primary Examiner*—John L. LeGuyader
*Assistant Examiner*—Andrew Wang
*Attorney, Agent, or Firm*—David G. Conlin; Ronald I. Eisenstein; David R. Resnick

[57] ABSTRACT

We have now discovered that eukaryotes, including mammals, have a gene that encodes a multifunctional protein having helicase activity, DNA repair activity, p53 sequestering activity and oncogenetic transformation potential. Enhanced transcripts and expression of this gene in non-testicular cells have a high correlation to disease state in a number of cancers, such as colorectal carcinomas, hereditary cancers resulting from defects in DNA repair pathways, breast cancers, etc. Accordingly, discovering enhanced levels of transcript or gene product in non-testicular tissues can be diagnostic of a predisposition to cancer, and prognostic for a particular cancer.

13 Claims, 25 Drawing Sheets

```
AATTCGGCAC GAGGCTGTCG AAAGTTTTAC TATAATGAAA GATATTTTCA TACTCTCAAA    60

AATATAGAGG AAAGGGGCCA AGATTATAGT ACCAGTCACA ATCTTTTGAT GAGGACGAA    119

ATG AAT CAG GTA ACA GAC TGG GTT GAC CCA TCA TTT GAT GAT TTT CTA   167
Met Asn Gln Val Thr Asp Trp Val Asp Pro Ser Phe Asp Asp Phe Leu
 1               5              10      CK2          15

GAG TGT AGT GGC GTC TCT ACT ATT ACT GCC ACA TCA TTA GGT GTG AAT   215
Glu Cys Ser Gly Val Ser Thr Ile Thr Ala Thr Ser Leu Gly Val Asn
             20              25              30

AAC TCA AGT CAT AGA AGA AAA AAT GGG CCT TCT ACA TTA GAA AGC AGC   263
Asn Ser Ser His Arg Arg Lys Asn Gly Pro Ser Thr Leu Glu Ser Ser
         35 PKC         40          CK2  45      PKC

AGA TTT CCA GCG AGA AAA AGA GGA AAT CTA TCT TCC TTA GAA CAG ATT   311
Arg Phe Pro Ala Arg Lys Arg Gly Asn Leu Ser Ser Leu Glu Gln Ile
     50              55           60      CK2

TAT GGT TTA GAA AAT TCA AAA GAA TAT CTG TCT GAA AAT GAA CCA TGG   359
Tyr Gly Leu Glu Asn Ser Lys Glu Tyr Leu Ser Glu Asn Glu Pro Trp
 65              70              75      CK2      80

GTG GAT AAA TAT AAA CCA GAA ACT CAG CAT GAA CTT GCT GTG CAT AAA   407
Val Asp Lys Tyr Lys Pro Glu Thr Gln His Glu Leu Ala Val His Lys
             85          CK2  90                      95

AAG AAA ATT GAA GAA GTC GAA ACC TGG TTA AAA GCT CAA GTT TTA GAA   455
Lys Lys Ile Glu Glu Val Glu Thr Trp Leu Lys Ala Gln Val Leu Glu
            100             105             110

AGG CAA CCA AAA CAG GGT GGA TCT ATT TTA TTA ATA ACA GGT CCT CCT   503
Arg Gln Pro Lys Gln Gly Gly Ser Ile Leu Leu Ile Thr Gly Pro Pro
            115             120             125     ATP

GGA TGT GGA AAG ACA ACG ACC TTA AAA ATA CTA TCA AAG GAG CAT GGT   551
Gly Cys Gly Lys Thr Thr Thr Leu Lys Ile Leu Ser Lys Glu His Gly
            130 BINDING SITE  135  PKC          140
                              *

ATT CAA GTA CAA GAG TGG ATT AAT CCA GTT TTA CCA GAC TTC CAA AAA   599
Ile Gln Val Gln Glu Trp Ile Asn Pro Val Leu Pro Asp Phe Gln Lys
145             150             155             160

GAT GAT TTC AAG GGG ATG TTT AAT ACT GAA TCA AGC TTC CAT ATG TTT   647
Asp Asp Phe Lys Gly Met Phe Asn Thr Glu Ser Ser Phe His Met Phe
            165             170             175
```

F I G. 4A

| | | | | | | | | | | | | | | | |
|---|---|---|---|---|---|---|---|---|---|---|---|---|---|---|---|
| CCC | TAT | CAG | TCT | CAG | ATA | GCA | GTT | TTC | AAA | GAG | TTT | CTA | CTA | AGA | GCG | 695 |
| Pro | Tyr | Gln | Ser | Gln | Ile | Ala | Val | Phe | Lys | Glu | Phe | Leu | Leu | Arg | Ala |
| | | | 180 | | | | 185 | | | | | | 190 | | |

ACA AAG TAT AAC AAG TTA CAA ATG CTT GGA GAT GAT CTG AGA ACT GAT  743
Thr Lys Tyr Asn Lys Leu Gln Met Leu Gly Asp Asp Leu Arg Thr Asp
          195               200               205      PKC

AAG AAG ATA ATT CTG GTT GAA GAT TTA CCT AAC CAG TTT TAT CGG GAT  791
Lys Lys Ile Ile Leu Val Glu Asp Leu Pro Asn Gln Phe Tyr Arg Asp
     210              215              220

TCT CAT ACT TTA CAT GAA GTT CTA AGG AAG TAT GTG AGG ATT GGT CGA  839
Ser His Thr Leu His Glu Val Leu Arg Lys Tyr Val Arg Ile Gly Arg
225     CK2     230              235                   240

TGT CCT CTT ATA TTT ATA ATC TCG GAC AGT CTC AGT GGA GAT AAT AAT  887
Cys Pro Leu Ile Phe Ile Ile Ser Asp Ser Leu Ser Gly Asp Asn Asn
              245              250              255

CAA AGG TTA TTG TTT CCC AAA GAA ATT CAG GAA GAG TGT TCT ATC TCA  935
Gln Arg Leu Leu Phe Pro Lys Glu Ile Gln Glu Glu Cys Ser Ile Ser
          260              265              270

AAT ATT AGT TTC AAC CCT GTG GCA CCA ACA ATT ATG ATG AAA TTT CTT  983
Asn Ile Ser Phe Asn Pro Val Ala Pro Thr Ile Met Met Lys Phe Leu
        275              280              285

AAT CGA ATA GTG ACT ATA GAA GCT AAC AAG AAT GGA GGA AAA ATT ACT 1031
Asn Arg Ile Val Thr Ile Glu Ala Asn Lys Asn Gly Gly Lys Ile Thr
    290              295              300

GTC CCT GAC AAA ACT TCT CTA GAG TTG CTC TGT CAG GGA TGT TCT GGT 1079
Val Pro Asp Lys Thr Ser Leu Glu Leu Leu Cys Gln Gly Cys Ser Gly
305   CK2       CK2 310              315                   320

GAT ATC AGA AGT GCA ATA AAC AGC CTC CAG TTT TCT TCT TCA AAA GGA 1127
Asp Ile Arg Ser Ala Ile Asn Ser Leu Gln Phe Ser Ser Ser Lys Gly
              325              330     PKC         335
                                                    CK2

GAA AAC AAC TTA CGG CCA AGG AAA AAA GGA ATG TCT TTA AAA TCA GAT 1175
Glu Asn Asn Leu Arg Pro Arg Lys Lys Gly Met Ser Leu Lys Ser Asp
              340 NLS     345         PKC     350

GCT GTG CTG TCA AAA TCA AAA CGA AGA AAA AAA CCT GAT AGG GTT TTT 1223
Ala Val Leu Ser Lys Ser Lys Arg Arg Lys Lys Pro Asp Arg Val Phe
              355     PKC     360 NLS     365

GAA AAT CAA GAG GTC CAA GCT ATT GGT GGC AAA GAT GTT TCT CTG TTT 1271
Glu Asn Gln Glu Val Gln Ala Ile Gly Gly Lys Asp Val Ser Leu Phe
        370              375              380

FIG. 4B

```
CTC TTC AGA GCT TTG GGG AAA ATT CTA TAT TGT AAA AGA GCA TCT TTA      1319
Leu Phe Arg Ala Leu Gly Lys Ile Leu Tyr Cys Lys Arg Ala Ser Leu
385                 390                 395cAMP PHOSPHO SITE400

ACA GAA TTA GAC TCA CCT CGG TTG CCC TCT CAT TTA TCA GAA TAT GAA      1367
Thr Glu Leu Asp Ser Pro Arg Leu Pro Ser His Leu Ser Glu Tyr Glu
CK2 CK2         405 PKC             410         CK2     415

CGG GAT ACA TTA CTT GTT GAA CCT GAG GAG GTA GTA GAA ATG TCA CAC      1415
Arg Asp Thr Leu Leu Val Glu Pro Glu Glu Val Val Glu Met Ser His
             420             425             430

ATG CCT GGA GAC TTA TTT AAT TTA TAT CTT CAC CAA AAC TAC ATA GAT      1463
Met Pro Gly Asp Leu Phe Asn Leu Tyr Leu His Gln Asn Tyr Ile Asp
        435                 440                 445

TTC TTC ATG GAA ATT GAT GAT ATT GTG AGA GCC AGT GAA TTT CTG AGT      1511
Phe Phe Met Glu Ile Asp Asp Ile Val Arg Ala Ser Glu Phe Leu Ser
    450                 455                 460

TTT GCA GAT ATC CTC AGT GGT GAC TGG AAT ACA CGC TCT TTA CTC AGG      1559
Phe Ala Asp Ile Leu Ser Gly Asp Trp Asn Thr Arg Ser Leu Leu Arg
465 CK2             470                 475                 480

GAA TAT AGC ACA TCT ATA GCT ACG AGA GGT GTG ATG CAT TCC AAC AAA      1607
Glu Tyr Ser Thr Ser Ile Ala Thr Arg Gly Val Met His Ser Asn Lys
                485                 490             495 PKC

GCC CGA GGA TAT GCT CAT TGC CAA GGA GGA GGA TCA AGT TTT CGA CCC      1655
Ala Arg Gly Tyr Ala His Cys Gln Gly Gly Gly Ser Ser Phe Arg Pro
            500             505                 510 PKC

TTG CAC AAA CCT CAG TGG TTT CTA ATA AAT AAA AAG TAT CGG GAA AAT      1703
Leu His Lys Pro Gln Trp Phe Leu Ile Asn Lys Lys Tyr Arg Glu Asn
        515                 520                 525

TGC CTG GCA GCA AAA GCA CTT TTT CCT GAC TTC TGC CTA CCA GCT TTA      1751
Cys Leu Ala Ala Lys Ala Leu Phe Pro Asp Phe Cys Leu Pro Ala Leu
        530                 535             540

TGC CGC CAA ACT CAG CTA TTG CCA TAC CTT GCT CTA CTA ACC ATT CCA      1799
Cys Arg Gln Thr Gln Leu Leu Pro Tyr Leu Ala Leu Leu Thr Ile Pro
545                 550                 555                 560

ATG AGA AAT CAA GCT CAG ATT TCT TTT ATC CAA GAT ATT GGA AGG CTC      1847
Met Arg Asn Gln Ala Gln Ile Ser Phe Ile Gln Asp Ile Gly Arg Leu
                565                 570                 575

CCT CTG AAG CGA CAC TTT GGA AGA TTG AAA ATG GAA GCC CTG ACT GAC      1895
Pro Leu Lys Arg His Phe Gly Arg Leu Lys Met Glu Ala Leu Thr Asp
            580                 585                 590 PKC
```

FIG. 4C

```
AGG GAA CAT GGA ATG ATA GAC CCT GAC AGC GGA GAT GAA GCC CAG CTT   1943
Arg Glu His Gly Met Ile Asp Pro Asp Ser Gly Asp Glu Ala Gln Leu
CK2     595                 600         CK2         605

AAT GGA GGA CAT TCT GCA GAG GAA TCT CTG GGT GAA CCC ACT CAA GCC   1991
Asn Gly Gly His Ser Ala Glu Glu Ser Leu Gly Glu Pro Thr Gln Ala
            610     CK2     615 CK2         620

ACT GTG CCG GAA ACC TGG TCT CTT CCT TTG AGT CAG AAT AGT GCC AGT   2039
Thr Val Pro Glu Thr Trp Ser Leu Pro Leu Ser Gln Asn Ser Ala Ser
625     CK2         630             635         CK2     640

GAA CTG CCT GCT AGC CAG CCC CAG CCC TTT TCA GCC CAA GGA GAC ATG   2087
Glu Leu Pro Ala Ser Gln Pro Gln Pro Phe Ser Ala Gln Gly Asp Met
                645                 650             655

GAA GAA AAC ATA ATA ATA GAA GAC TAC GAG AGT GAT GGG ACA T         2130
Glu Glu Asn Ile Ile Ile Glu Asp Tyr Glu Ser Asp Gly Thr *
            660             665             670

AGAAGCCAGC CTGCTAATCA GATTGCTACT TCACAGCTTC ATTTTTGTTT CATTCAGTGG 2190
TACTTCAGCA GAGTTAATAT GCTTTTCTGA TGAATTACAC AACAGTTTGT TAATTCTTCA 2250
TTCTTGTAGT ATTTCATCAC AAGAAACCTA CTCTTCTGTC ATCTTGAAGT AAATAGAAGA 2310
TCAAGCCTTC AAATCTCTTA ATTTTTTCGG TATTTATTAA ATCTGTGAGT GGTTTAAGGA 2370
GCGGTCAGTG TGTATAAAGT GTGTTTGAAC ATTATGCCAA ATATCAAGAT GTGAAGGACT 2430
AATTCAGGAT GCAAAAACGT TATTGGGGGG TTGTAAATAT CAACTATTCA ACAGTTTAGG 2490
ATGCAATTAC GAGTGTAAAC TGTGTGCCTT ATTTACACTT TATTGTCTCC CGCTTCTCAG 2550
ATAGTTTTGA TGTGTTGTAC AGTGGAATAT CTTAGATACT TTTTGGAAAG TATTTACATA 2610
AGTTATATCA CAATTAAAAT GTTGAATTTC TCGTGCCGAA TT                    2652
```

FIG. 4D

| | |
|---|---|
| TAH 85-164 | KPETQHELAVHKKIEEVETWLKAQVLERQPKQGGSILLITGPPGCGKTTTLKILSKEHGIQVQEWINPVLPDFQKDDFK |
| RuvB(E) 24-98 | RPKLLEEYVGQPQVRSQMEIFIKAAKL---RGDALDHLLIFGPPGLGKTTLANIVANEMGVNLRTTSGPVLEK--AGDLA |
| TAH 165-237 | GMFNTESSFH-MF--PYQSQIAVFKEFLLRA-TKYNKLQMLGDDLRTDK-KIILVE-DLPNQFYRDSHTLHEVLR-KYVR |
| RuvB(E) 99-177 | AMLTNLEPHDVLFIDEIHRLSRVVEEVLYPAMEDYQLDIMIGEGPAARSIKIDLPPFTLIGATTRAG-SLTSPLRDRFGI |
| TAH 238-314 | IGRCPLIFIISDSLSGDNNQRLLFPKETQEECSISNISFNPVAPTIMKFLNRIVTIEANKNGGKITVP-DKTSLELL |
| RuvB(E) 178-254 | VQRLEFYQVPDLQYIVSRSARFM-GLEMSDDGALEVARRARGTPRIANRLLRRVRDFAEVKHDGTISADIAAQALDML |

FIG. 5

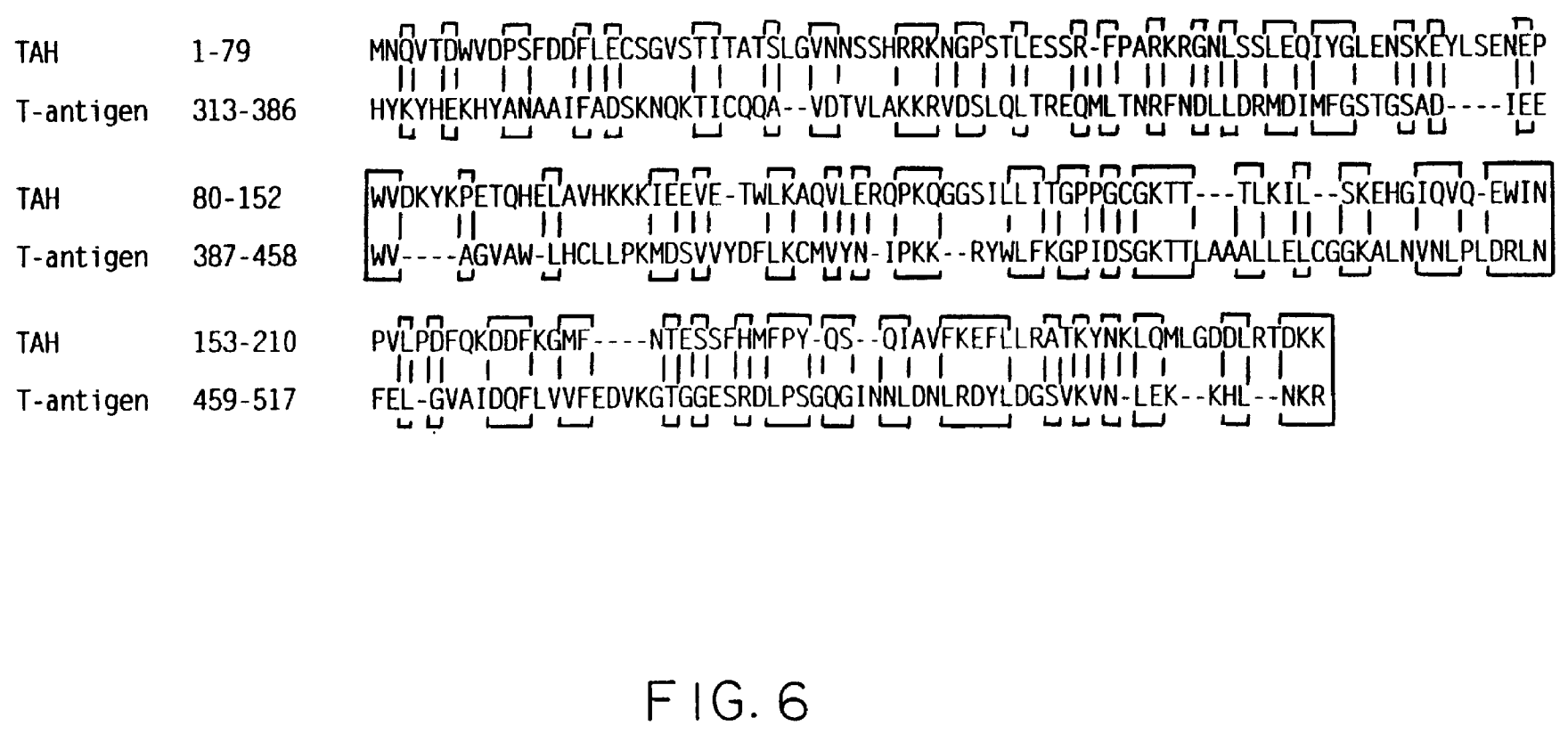

| | | |
|---|---|---|
| TAH | 1-79 | MNQVTDWVDPSFDDFLECSGVSTTTATSLGVNNSSHRRKNGPSTLESSR-FPARKRGNLSSLEQIYGLENSKEYLSENEP |
| T-antigen | 313-386 | HYKYHEKHYANAAIFADSKNQKTICQQA--VDTVLAKKRVDSLQLTREQMLTNRFNDLLDRMDIMFGSTGSAD----IEE |
| TAH | 80-152 | WDKYKPETQHELAVHKKKIEEVE-TWLKAQVLEROPKQGGSILLITGPPGGKTT----TLKIL--SKEHGIQVQ-EWIN |
| T-antigen | 387-458 | W-----AGVAW-LHCLLPKMDSVVYDFLKCMVYN-IPKK--RYWLFKGPIDSGKTT LAAALLELCGGKALNVNLPLDRLN |
| TAH | 153-210 | PVLPDFQKDDFKGMF----NTESSFHMFPY-QS--QIAVFKEFLLRATKYNKLQMLGDDLRTDKK |
| T-antigen | 459-517 | FEL-GVAIDQFLVVFEDVKGTGGESRDLPSGQGINNLDNLRDYLDGSVKVN--LEK--KHL--NKR |

FIG. 6

```
TAH      339   NLRPRKKGMSLKSDAVLSKSKRRKKPDRVFENQEVQAIGGKDVSLFLFRA
               ::|:  .|:|  ..:   |:||  :   ::.::||:. ...:||  ::
ERCC6     46   SFRSVGDGLSTSAVGCASAAPRRGPALLHIDRHQIQAVEPSAQALEL-QG

TAH      389   LGKILYCKRASLTELDSPRLPSHLSEYERDTLLVEPE              425
               |  :| ..:.|.:  ..: :  :| .|.: ||: |
ERCC6     95   LGVDVY-DQDVLEQGVLQQVDNAIHEASRASQLVDVE              130
```

FIG. 7

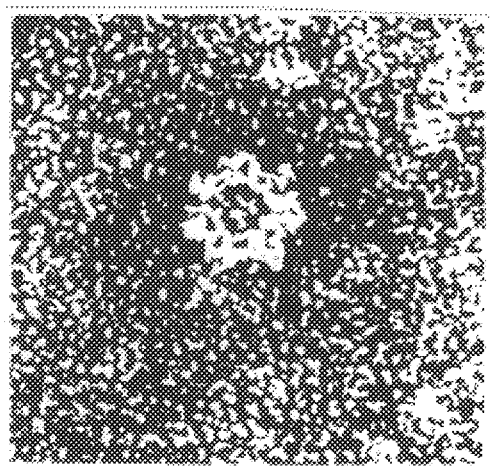
FIG. 13A
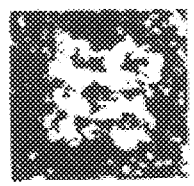   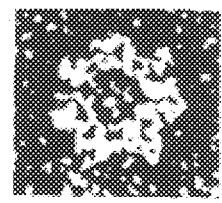
FIG. 13B   FIG. 13C

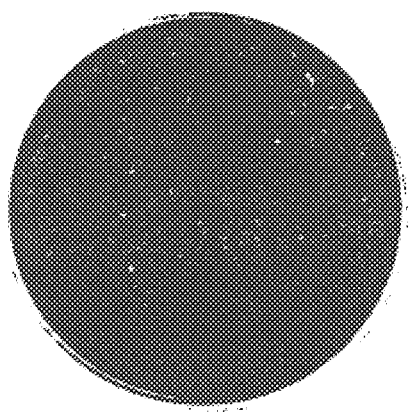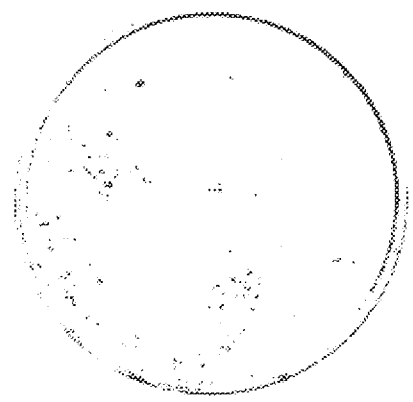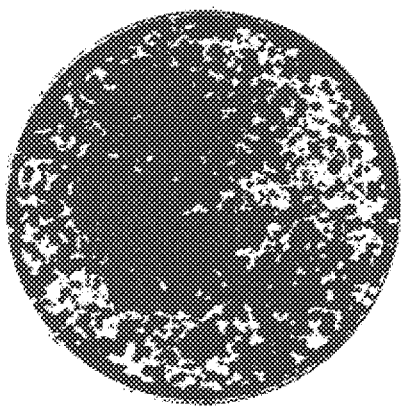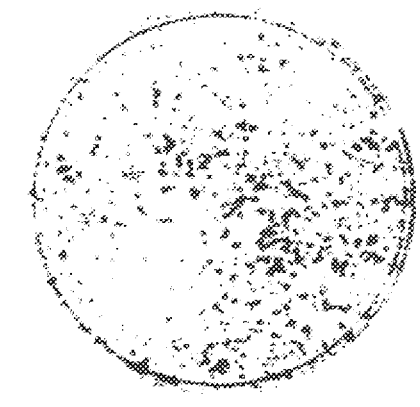
FIG. 23 A    FIG. 23 B

CANCER ASSOCIATED GENE PROTEIN EXPRESSED THEREFROM AND USES THEREOF

FIELD OF THE INVENTION

The present invention pertains to a eukaryotic DNA gene, the protein expressed therefrom, and uses thereof, for example, in drug screening, cancer prognosis and diagnosis. More specifically, the invention relates to detection of alterations in the expression of this gene associated with a variety of human cancers, such as colon cancer, breast cancer, etc.

BACKGROUND OF THE INVENTION

Alterations in cellular function arise from a wide range of sources. Certain changes are associated with the malignant transformation of a cell. In some cases the change is triggered by cellular factors, in other situations the alteration brings about the malignant transformation. One class of molecules associated with malignant transformation are oncogenes. For example, a mutation in a normal gene can result in the malignant transformation of a cell such as when the proto-oncogene ras is transformed by a point mutation at, for example, amino acid 13 to become an oncogene. Other types of changes from proto-oncogenes to oncogenes can result from the enhanced expression of gene such as with neu/erbB2. The simian virus 40 (SV40) T-antigen is another oncogene expression product that displays a wide range of functions. [Fanning, E., and Knippers, R., Annul. Rev. Biochem. 61:55–85 (1993)]. It can perform functions including replication, transcriptional regulation as well as cellular transformation. This 708 amino acid protein has a number of functional domains, including those providing helicase activity, ATPase activity and sites for binding DNA polymerase α-primase, and the retinoblastoma and p53 suppressor genes, as well as [Ibid.]. These binding sites influence function, for example, SV40 T-antigen is believed to have p53 sequestering activity.

Another class of molecules associated with malignant transformation are tumor-suppressor genes, such as the p53 gene, the retinoblastoma gene and the Wilm's tumor gene. The normal expression of these genes typically prevents unchecked cellular growth, while their mutation allows growth to go unchecked, thereby resulting in malignant transformation of a cell. Considerable attention has focused on all of the members of this family, particularly p53. p53 has been called at various times the "guardian of the genome" or "gate keeper" because of its complex role in cellular regulation. For example, p53 can control cell growth and division, push cells into a programmed self-destruct sequence and prevent undesired amplification of DNA. [Science 262:1958–1961 (1993)]. Mutations in this gene have been associated with a wide range of human tumors, including the bladder, brain, breast, cervix, colon, esophagus, larynx, liver, lung, ovary, pancreas, prostate, skin, stomach, and thyroid.

p53 has been reported to interact with a wide range of molecules, which in turn effect p53 functioning. For example, its binding to an oncogene such as the SV40 T-antigen results in a loop whereby p53 provides an anti-helicase effect, but is in turn removed from being able to regulate growth. p53 has also been reported to recognize damaged DNA, exhibit an anti-helicase activity, be inducible by UV light and regulates expression of DNA excision repair gene, such as GADD45. Consequently, many people believe that p53 shows how tumor suppressor gene pathways and DNA repair systems interact.

Members of DNA repair systems are additional molecules that can dramatically effect a cell, particularly the malignant transformation of a cell. For example, it was recently discovered that a mismatch repair system exists in humans [Fishel, R, et al., Cell 75:1027–1038 (1993); Leach, F. S., et al., Cell 75:1215–1225 (1993); and Parsons, R., Cell 75:1227–1236 (1993)). Members of this system include the human mismatch repair gene hMSH2. Mutations in these genes have been associated with a variety of cancers including hereditary non-polyposis colon cancer (HNPCC) (Aaltonen, L. A., Science 260:812–816 (1993)]. A variety of DNA repair systems have been shown to play essential roles in the maintenance of the proper DNA sequence required for an organism is survival and propagation. For example, studies in E. coli have shown that in conjunction with RecA, the RuvABC complex mediates recombinational repair utilizing RuvA as a DNA-binding protein and RuvB as an ATP-dependent helicase to promote branch migration of Holliday junction, and RuvC, as a resolvase to resolve this junction. However the eukaryotic equivalent of the RuvABC system has not yet been identified.

In DNA replication and repair the ability to unwind the double-stranded DNA is necessary in order to provide single-stranded DNA as a template. One class of enzymes that accomplish this function are referred to as helicases, which act by disrupting the hydrogen bonds that hold the two strands of duplex DNA together. Helicases have been found in a wide range of organisms including E. coli, yeast, calf, lily, mouse, and frogs [Matson, S. W. and Kaiser-Rogers, K. A., Annul. Rev. Biochem. 59:289–329 (1990)]. There are a wide range of helicases. For example, there are at least 10 enzymes capable of unwinding double-stranded nucleic acid in E. coli alone [Ibid.].

The use of cellular markers for both diagnostic and prognostic measurement of cellular alteration is of considerable importance. One problem with monitoring malignant cells is that many markers associated with malignant transformation are the result of mutations. Accordingly, one needs to use probes that can distinguish the mutation from the normal, and in a number of cases, determine what the specific mutation is. Thus, discovering a cellular marker associated with a wide range of malignancies that results from over-expression of the gene product, rather than its mutation would provide many advantages in diagnostic and prognostic screens. For example, one could use a reduced number of probes because one does not have to be worry about differentiating between various mutations, but only with measuring level of expression.

Further, the cloning and expression of this marker, particularly if associated with the malignant transformation of a cell, can be used to transform cells, and create stable and transient cell lines that can be used in drug screening. Additionally, they can be used for therapeutics, such as anti-sense therapy, etc. We have now discovered that eukaryotes, including mammals, have a gene referred to herein as testis-associated helicase (TAH) that encodes a multifunctional protein having helicase activity, DNA repair activity, p53 sequestering activity and oncogenic transformation potential. Enhanced transcripts and expression of this gene in non-testicular cells have a high correlation to disease state in a number of cancers, such as colorectal carcinomas, hereditary cancers resulting from defects in DNA repair pathways, breast cancers, etc. Accordingly, discovering enhanced levels of transcript or gene product in non-testicular tissues can be diagnostic of a predisposition to cancer, and prognostic for a particular cancer.

SUMMARY OF THE INVENTION

We have now discovered that eukaryotes, including mammals, have a gene that encodes a multifunctional protein having helicase activity, DNA repair activity, p53 sequestering activity and oncogenetic transformation potential. Enhanced transcripts and expression of this gene in non-testicular cells have a high correlation to disease state in a number of cancers, such as colorectal carcinomas, hereditary cancers resulting from defects in DNA repair pathways, breast cancers, etc. Accordingly, discovering enhanced levels of transcript or gene product in non-testicular tissues can be diagnostic of a predisposition to cancer, and prognostic for a particular cancer.

We have discovered and sequenced this gene in humans. As will be discussed below, this gene has many applications. It can be used in assays, to express gene product, for drug screens, and therapeutically.

BRIEF DESCRIPTION OF THE DRAWINGS

FIGS. 4A–4D present the nucleotide (SEQ ID NO:1) and deduced amino acid sequence (SEQ ID NO:2) of full-length TAH. FIGS. 4A–4D represents the four sheets that make up the sequence. The open reading frame encodes a 670 amino acid sequence containing a typical ATP or GTP binding site (boxed). Two putative nuclear localization signals (NLS) are indicated. A phosphorylation site for protein kinase (PKC) at ATP binding site and other PKC sites are shown. Phosphorylation sites for cacisen kinase II (CK2) are indicated.

FIG. 5 illustrates significant homology between TAH and RuvB, a DNA helicase involved in DNA recombination repair in E. coli. TAH and RuvB share 21% identity and 40% conservation in 238 amino acid sequence.

FIG. 6 illustrates homology between TAH and SV40 large tumor antigen, a P53 and RB binding protein having DNA and RNA helicase activities.

FIG. 7 illustrates homology between TAH and ERCC6, a DNA helicase involved in excision repair.

FIGS. 13A–C show TAH protein structure revealed by electron microsopy. Negative-stained TAH shows a hexamer-based donut shape, could be a quadruple-hexamer. FIG. 13A shows a donut shape. C, top view; B, side view.

FIGS. 23A and B illustrate that high level of TAH protein are related to resistance to γ-irradiation.

DETAILED DESCRIPTION

Figure 1:
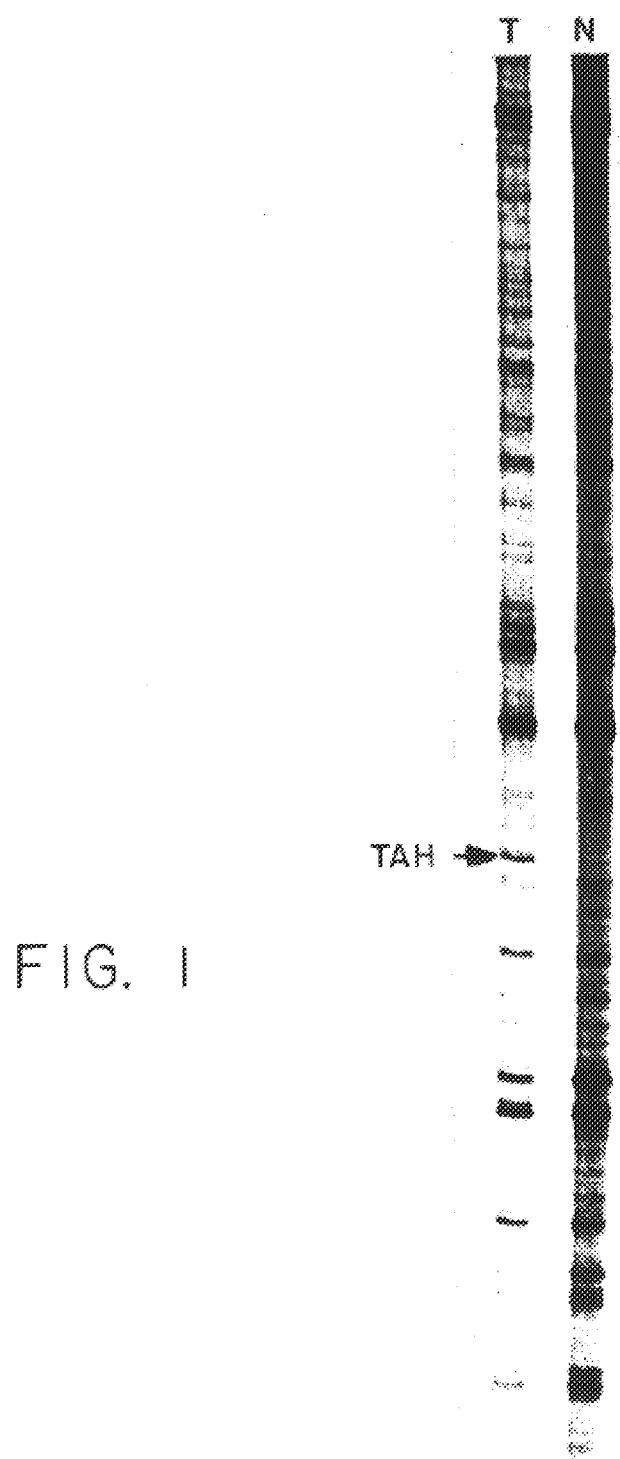
FIG. 1 shows identification of TAH cDNA from human carcinoma by Palindromic cDNA display.

We have now discovered that eukaryotes, including mammals, have a gene that encodes a multi-functional protein having helicase activity, DNA repair activity, p53 sequestering activity and oncogenic transformation potential. In humans this gene is normally expressed in large quantities only in the testes. However, alterations of this gene such as its enhanced expression in other tissues are associated with the malignant transformation of such cells. Such a phenotype of enhanced levels of transcript and/or expression has a high correlation to disease state in a number of cancers, such as colorectal carcinomas, hereditary cancers resulting from defects in DNA repair pathways, breast cancers, ovarian cancers, cervical cancers, prostate cancer, colon cancers. Accordingly, discovering enhanced levels of transcript and/or expression of this gene can be diagnostic of a predisposition to cancer, and prognostic for a particular cancer.

The diagnostic and prognostic methods of the present invention include looking at alterations of this gene in tissues and cellular fluid. Preferably, the gene is looked at in a mammal, most preferably a human. The alteration may be due to a deletion, addition and/or mutation, such as a point mutation, or enhanced levels of expression of this gene. Preferably, the alteration is enhanced expression of the gene. The changes resulting from these alterations are also reflected in the resultant protein and mRNA as well as the gene.

Consequently, one aspect of this invention involves determining whether there is an alteration of the gene or its expression product, preferably one screens for enhanced expression. This determination can involve screening for the gene, its mRNA, its gene products. Alterations can be detected by screening in a suitable sample obtained, for example, from tissue, human biological fluid, such as blood, serum, plasma, urine, cerebrospinal fluid, supernatant from normal cell lysate, supernatant from preneoplastic cell lysate, supernatant from neoplastic cell lysate, supernatants from carcinoma cell lines maintained in tissue culture, eukaryotic cells, etc. The gene and gene products are typically present in the nucleus of a cell. However, as the gene's expression increases, certain cells die releasing the cellular contents including the gene, its gene product and mRNA resulting in enhanced levels throughout the organism. Preferably, one screens cells of interest for the gene, gene product or mRNA.

It is helpful to isolate the tissue free from surrounding normal tissues for screening. Means for enriching a tissue preparation for tumor cells are known in the art. For example, the tissue may be isolated from paraffin or cryostat sections. Cancer cells may also be separated from normal cells by flow cytometry. These as well as other techniques for separating tumor from normal cells are well known in the art. It is then helpful to screen normal tissue free from malignant tissue. Then comparisons can be made to determine whether a different level of expression is seen.

Expression levels can be detected by a wide range of methods. For example, one can use a probe, either an antibody or nucleotide, to screen for the wild type TAH gene product, gene or mRNA. A preferred assay method includes using an antibody to the protein such as an ELISA, Western blot, etc. One can determine relative levels of DNA or mRNA by a wide range of methods including Northern blot, Southern blot, etc.

Detection of mutations may be accomplished by molecular cloning of the TAH gene present in the tumor tissue such as a testicular tumor and sequencing the gene using techniques well known in the art. For example, mRNA can be isolated, reverse transcribed and the cDNA sequenced. Alternatively, the polymerase chain reaction can be used to amplify the TAH gene or fragments thereof directly from a genomic DNA preparation from the tumor tissue. The DNA sequence of the amplified sequences can then be determined. Alternatively, one can screen for marker portions of the DNA that are indicative of changes in the DNA. The polymerase chain reaction itself is well known in the art. See e.g., Saiki et al., Science, 239:487 (1988); U.S. Pat. No. 4,683,203; and U.S. Pat. No. 4,683,195. Specific primers which can be used in order to amplify the TAH genes will be discussed in more detail below.

Specific deletions can also be detected. For example, restriction fragment length polymorphism (RFLP) probes for the TAH genes, can be used to score loss of a wild-type allele. Other techniques for detecting deletions, as are known in the art, can be used.

Loss of wild-type TAH function may also be detected on the basis of the loss of a wild-type expression product of the gene. Preferably, one would look at testicular tissue for such a change because TAH is typically expressed at these high levels. Such expression products include both the mRNA as well as the protein product itself. For example, one could look at inactivation of certain protein function, e.g. inactivation a helicase activity, changes that result in loss of binding sites or reduction of binding affinity at binding sites, e.g. p53 binding site, ATP binding site. Point mutations may be detected by sequencing the mRNA directly or via molecular cloning of cDNA made from the mRNA. The sequence of the cloned cDNA can be determined using DNA sequencing techniques which are well known in the art. Alternatively, one can screen for changes in the protein. For example, a panel of antibodies, for example single chain or monoclonal antibodies, could be used in which specific epitopes involved are represented by a particular antibody. Loss or perturbation of binding of a monoclonal antibody in the panel would indicate mutational alteration of the protein and thus of the gene itself. Alternatively, deletional mutations leading to expression of truncated proteins can be quickly detected using a sandwich type ELISA screening procedure, in which, for example, the capture antibody is specific for the N-terminal portion of the pathway protein. Failure of a labeled antibody to bind to the C-terminal portion of the protein provides an indication that the protein is truncated. Even where there is binding to the C-terminal, further tests on the protein can indicate changes. For example, molecular weight comparison. Any means for detecting altered TAH can be used to detect loss of wild-type TAH. Loss of a wild function can be indicative that other host cells will be less likely to survive apoptosis. Accordingly, malignant cells are less likely to survive and spread resulting in less tumor. Therefore, individuals possessing such an alteration are likely to be less prone to developing cancer then other individuals. In male screening testicular tissue is preferred. However, any tissue can be screened to determine if there is an alteration.

Alternatively, mismatch detection can be used to detect point mutations in the TAH gene or its mRNA product. While these techniques are less sensitive than sequencing, they can be simpler to perform on a large number of tumors. An example of a mismatch cleavage technique is the RNAase protection method, which is described in detail in Winter et al., Proc. Natl. Acad. Sci. U.S.A., 82:7575 (1985) and Meyers et al., Science, 230:1242 (1985). In the practice of the present invention, the method involves the use of a labeled riboprobe which is complementary to the human TAH. The riboprobe and either mRNA or DNA-isolated form the tumor tissue are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full-length duplex RNA for the riboprobe and the TAH mRNA or DNA. Where the riboprobe comprises only a segment of the TAH or gene it will be desirable to use a number of these probes to screen the whole mRNA sequence for mismatches.

In similar fashion, DNA probes can be used to detect mismatches, through enzymatic or chemical cleavage. See, e.g., Cotton et al., Proc. Nat. Acad. Sci. U.S.A., 85:4397 (1988); and Shenk et al., Proc. Natl. Acad. Sci. U.S.A., 72:989 (1975). Alternatively, mismatches can be detected by shifts in the electrophoretic mobility of mismatched duplexes relative to matched duplexes. See, e.g., Cariello, Human Genetics, 42:726 (1988). With either riboprobes or DNA probes, the cellular mRNA or DNA which might contain a mutation can be amplified using PCR before hybridization.

The TAH gene or gene product can be detected in a wide range of biological samples, such as serum, stool, or other body fluids, such as urine and sputum. The same techniques discussed above can be applied to all biological samples. By screening such biological samples, a simple early diagnosis can be achieved for many types of cancers. Even when someone has been diagnosed with cancer, these screens can be prognostic of the condition, e.g., by looking at the absolute level of TAH gene or gene product. The prognostic method of the present invention is useful for clinicians so that they can decide upon an appropriate course of treatment.

The methods of screening of the present invention are applicable to any sample in which alterations in TAH have a role, such as in tumorigenesis.

The method of the present invention for diagnosis of a TAH associated-tumor is applicable across a broad range of tumors. These include breast, prostate, colorectal, ovary, endometrial (uterine), renal, bladder, skin, rectal and small bowel.

The present invention also provides a kit useful for determination of alterations of the TAH gene for example using a method of DNA amplification, e.g., the polymerase chain reaction. The kit comprises a set of pairs of single stranded oligonucleotide DNA primers which can be annealed to sequences within or surrounding the TAH gene in order to prime amplifying DNA synthesis of the gene itself. Another kit involves the use of antibodies for the gene product.

The antibody probes can be monoclonal, polyclonal or single chain antibodies, although monoclonal antibodies are preferred. Furthermore, as used herein, the term antibody includes whole immunoglobulin as well as antigenic binding fragments (i.e. immunoreactive fragments) thereof, which display the above characteristics. The antibody is preferably generated to native TAH protein, although one can prepare an immunogenic peptide that contains a specific epitope of TAH and use that to generate the antibody. Such peptides can be synthesized by conventional means. The antibodies can be prepared by techniques well known to the skilled artisan. For example, the protein or an antigenic portion thereof can be conjugated to keyhole limpet hemocyanin (KLH) and used to raise an antibody in an animal such as a rabbit. Typically the peptide-KLH conjugate is injected several times over a period of about two months to generate antibodies. Antibodies are collected from serum by standard techniques and screened to find an antibody specific for the desired epitope of TAH. Monoclonal antibodies can be produced in cells which produce antibodies and used to generate monoclonal antibodies by using standard fusion techniques for forming hybridoma cells [Kohler, G., et al. *Nature* 256:495 (1975)]. Typically this involves fusing an antibody producing cell with an immortal cell line such as a myeloma cell to produce the hybrid cell. Alternatively, monoclonal antibodies can be produced from cells by the method of Huse, et al., *Science* 246:1275 (1989), both Kohler and Huse are incorporated herein by reference.

For example, hybridomas can be generated by immunization of mice with viable cells expressing TAH. Preferably, these cells express the full length protein, although partial domains can also be used. Using the full length protein as an immunogen, it is possible to generate a collection of monoclonal antibodies with specificities that span the entire length of the protein. This is as opposed to the use of peptide immunogens or short polypeptides generated by prokaryotic systems, which present a more limited number of epitopes from the original protein and hence raise an immune response of more limited specificity. Furthermore, the protein should not be fully denatured.

The mice, for example, SJL mice, can be immunized intraperitoneally (I.P.) with a sufficient number of viable cells of the host cell, which expresses essentially no TAH. Cyclophosphamide injection intraperitonially can be done one and two days following the primary injection. About two weeks following immunization, mice are then injected with a sufficient amount of transformed cells expressing high levels of TAH and then allowed another two weeks at which time the entire procedure is repeated. Alternatively, with for example SJL mice, there can be 12 I.P. injections of different types of cells, which, however, express the TAH, every 1–2 weeks. This would be followed with a single large injection of TAH or TAH-expressing cell. Four days following the last injection of the transformed cells, the animals are sacrificed and their spleens obtained for the first fusion.

Hybridomas are produced by fusing cells by standard techniques, such as from immunized mice with SP2/0 myeloma cells by a polyethylene glycol (PEG) method. Cells are aseptically removed from immunized mice and a single cell suspension of the spleen cells obtained by perfusing the spleen with serum-free media (e.g., DMEM). Spleen cells and myeloma cells are mixed together at a ratio, for example, of 5 to 1, spleen cells to myeloma cells. The cells are then centrifuged and the supernatant removed by aspiration. The cells are then grown in medium by standard techniques. Hybridomas, which grow after the fusion procedure, are then screened for secretion of antibodies which show high levels of binding to TAH and not other proteins. Screening can be done on fixed cells or cell lysates or by cell surface immunofluorescence staining of live cells. Hybridomas that produce positive results are expanded and cloned by limiting dilution to assure that the cells and resulting antibodies are indeed monoclonal. Hybridoma colonies that test positive for these characteristics and presumably the presence of antibody to TAH are diluted in media to a concentration of, for example, 0.5 hybridoma cells per milliliter. Once colonies grow, the supernatants are again tested for the presence of antibody to TAH. If the results are positive when tested by an ELISA assay, the colonies are cloned again by limiting dilution.

One preferred monoclonal antibody is HT-1 expressed by hybridoma 8A7-TAH. These antibodies including HT-1, can then be used to determine the amount of TAH in a sample by contacting the sample, either body fluid or tissue, preferably tissue with at least one of the antibodies, preferably a monoclonal antibody, and determining whether binding has occurred. See, for example, Table 1. Preferably, one quantifies the amount of binding that occurs. As aforesaid, immunoreactive fragments of these antibodies can also be used and are included within the definition of antibody as used herein.

The TAH is differentially expressed in normal and malignant tissues. Tumors expressing the highest levels of TAH frequently are derived from tissues which express high levels. Thus, one can locate tumors by looking for high levels of binding of the present antibody. Furthermore, it appears that the level of TAH expression increases in a tumor as disease state progresses. Thus, by monitoring the level of expression one can determine the prognosis and determine the most appropriate therapy.

Additionally, these antibodies can be used to locate, monitor and/or isolate cells in vivo which differentially express TAH. For example, the antibody can be labeled with a radionuclide, e.g., 111-indium, technetium-99m. The labelled antibody can then be injected intravenously and scanned to determine where the labelled antibody accumulates. Typically, it will differentially accumulate in cells producing high levels of TAH. The amount of labeled antibody can readily be determined based upon the present disclosure, and methods for scanning are well known in the art. For example, one can use a scintigraphic camera for scanning. By looking for cells having antibody binding, one can detect non-testicular cells expressing TAH, isolation can be accomplished by standard techniques.

In accord herewith, the presently described antibody or a cocktail of probes including antibodies to other proteins that one wishes to monitor at the same time such as a protein produced by and associated with a tumor can be used for detection. The antibody probes can be labeled directly with a reporter or indirectly with a specific binding pair using conventional techniques.

Specific binding pairs can be of the immune or non-immune type. Immune specific binding pairs are exemplified by antigen-antibody systems of hapten/anti-hapten systems. These include fluorescein/anti-fluorescein, dinitrophenyl/anti-dinitrophenyl, biotin/anti-biotin, peptide/anti-peptide and the like.

Non-immune binding pairs include systems wherein the two components share a natural affinity for each other but are not antibodies. Exemplary non-immune pairs are biotin-streptavidin, intrinsic factor-vitamin $B_{12}$, folic acid-folate binding protein and the like.

A variety of methods are available to covalently label antibodies with members of specific binding pairs. Methods are selected based upon the nature of the member of the specific binding pair, the type of linkage desired, and the tolerance of the antibody to various conjugation chemistries. Biotin can be covalently coupled to antibodies by utilizing commercially available active derivatives. Some of these are biotin-N-hydroxy-succinimide which binds to amine groups on proteins; biotin hydrazide which binds to carbohydrate moieties, aldehydes and carboxyl groups via a carbodiimide coupling; and biotin maleimide and iodoacetyl biotin which bind to sulfhydryl groups. Fluorescein can be coupled to protein amine groups using fluorescein isothiocyanate. Dinitrophenyl groups can be coupled to protein amine groups using 2,4-dinitrobenzene sulfate or 2,4-dinitrofluorobenzene. Other standard methods of conjugation can be employed to couple monoclonal antibodies to a member of a specific binding pair including dialdehyde, carbodiimide coupling, homofunctional crosslinking, and heterobifunctional crosslinking. Carbodiimide coupling is an effective method of coupling carboxyl groups on one substance to amine groups on another. Carbodiimide coupling is facilitated by using the commercially available reagent 1-ethyl-3-(dimethyl-aminopropyl)carbodiimide (EDAC).

Homobifunctional crosslinkers, including the bifunctional imidoesters and bifunctional N-hydroxy-succinimide esters, are commercially available and are employed for coupling amine groups on one substance to amine groups on another. Heterobifunctional crosslinkers are reagents which possess different functional groups. The most common commercially available heterobifunctional crosslinkers have an amine reactive N-hydroxysuccinimide ester as one functional group, and a sulfhydryl reactive group as the second functional group. The most common sulfhydryl reactive groups are maleimides, pyridyl disulfides and active halogens. One of the functional groups can be a photoactive aryl nitrene, which upon irradiation reacts with a variety of groups.

The detectably-labelled probe, e.g., antibody, detectably-labelled antibodies, or detectably-labelled member of the specific binding pair is coupled to a reporter which can be a radioactive isotope, enzyme, fluorogenic, chemiluminescent or electrochemical materials. Commonly used radioactive isotopes are $^{125}I$, $Tc^{99m}$ and $^3H$. Standard radioactive isotopic labeling procedures include the chloramine T, lactoperoxidase and Bolton-Hunter methods for $^{125}I$ and reduction methylation for $^3H$.

Enzymes suitable for use in this invention include, but are not limited to, horseradish peroxidase, alkaline phosphatase, β-galactosidase, glucose oxidase, luciferase, β-lactamase, urease and lysozyme. Enzyme labeling is facilitated by using dialdehyde, carbodiimide coupling, homobifunctional crosslinkers and heterobifunctional crosslinkers as described above for coupling an antibody with a member of a specific binding pair.

The labeling method chosen depends on the functional groups available on the enzyme and the material to be labeled, and the tolerance of both to the conjugation conditions. The labeling method used in the present invention can be one of, but not limited to, any conventional methods currently employed including those described by Engvall and Pearlmann, *Immunochemistry* 8:871 (1971), Avrameas and Ternynck, *Immunochemistry* 8:1175 (1975), Ishikawa et al., *J. Immunoassay* 4 (3):209–327 (1983) and Jablonski, *Anal. Biochem.* 148:199 (1985), which are incorporated by reference.

Labeling can be accomplished by indirect methods such as using spacers or other members of specific binding pairs. An example of this is the detection of a biotinylated antibody with unlabelled streptavidin and biotinylated enzyme, with streptavidin and biotinylated enzyme being added either sequentially or simultaneously. Thus, according to the present invention, the antibody used to detect can be detectably-labelled directly with a reporter or indirectly with a first member of a specific binding pair. When the antibody is coupled to a first member of a specific binding pair, then detection is effected by reacting the antibody-first member of a specific binding complex with the second member of the binding pair which is labelled or unlabelled as mentioned above.

Moreover, the unlabelled detector antibody can be detected by reacting the unlabelled antibody with a labelled antibody specific for the unlabelled antibody. Such an anti-antibody can be labelled directly or indirectly using any of the approaches discussed above. For example, the anti-antibody can be coupled to biotin which is detected by reacting with the streptavidin-horseradish peroxidase system discussed above.

One preferred embodiment utilizes biotin. The biotinylated antibody is in turn reacted with streptavidin-horseradish peroxidase complex. Orthophenylenediamine, 4-chloro-naphthol, or tetramethylbenzidine (TMB) can be used to effect chromogenic detection.

The preferred immunoassay format for practicing this invention is a forward sandwich assay in which the capture reagent has been immobilized, using conventional techniques, on the surface of the support. Suitable supports used in assays include synthetic polymer supports, such as polypropylene, polystyrene, substituted polystyrene, e.g., aminated or carboxylated polystyrene; polyacrylamides; polyamides; polyvinylchloride, etc.; glass beads; agarose; nitrocellulose, etc.

The present antibody can also be used therapeutically as a carrier for drugs, biologically and chemically produced toxins or cytotoxic agents. These antibodies will differentially locate cells expressing high levels of TAH and are an effective method of delivery. The drugs, toxins and cytotoxic materials can be attached to the antibody in the same manner as the other labels resulting in a coupled conjugate. In addition, the antibody TAH complex inhibits a wide variety of TAH function. For example, the addition of antibody to a system containing TAH prevents its helicase activity, its ATP/binding activity, etc. Thus, TAH antibodies can be used to inhibit the ability of the protein to bind to P53.

The antibody can be administered by a number of methods. One preferred method is set forth by Marasco and Haseltine in PCT WO94/02610, which is incorporated herein by reference. This method discloses the intracellular delivery of a gene encoding the antibody, in this case the TAH antibody. One would preferably use a gene encoding a single chain TAH antibody. The antibody would preferably contain a nuclear localization sequence, for example Pro-Lys-Lys-Lys-Arg-Lys-Val [Lawford, et al. *Cell* 46:575 (1986)]; Pro-Glu-Lys-Lys-lle-Lys-Ser [Stanton, et al., *Proc. Natl. Acad. Sci. USA* 83:1772 (1986)], Gln-Pro-Lys-Lys-Pro [Harlow, et al., *Mol. Cell. Biol.* 5:1605 (1985)]; Arg-Lys- Lys-Arg for the nucleus. One preferably uses an SV40 nuclear localization signal. By this method one can intracellularly express a TAH antibody, which can block TAH functioning in desired cells.

One can also use the TAH protein therapeutically. While its undesired expression can have adverse consequences, it also provides a number of benefits. For example, the protein enhances resistance to mutagenic agents such as UV light, chemicals. Although not wishing to be bound by theory we believe this results from the protein assisting in DNA repair from damage caused by these agents. We have shown, for example, that TAH can even enhance resistance to such agents in RuvB⁻ bacterial cells. TAH protein can be delivered by use of expression vectors encoding the protein or by delivering the protein in a delivery vehicle such as a liposome.

The probe, for example, antibody or peptide can be delivered by any of a number of means. For example, either can be administered by parenteral injection (intramuscular (i.m.), intraperitoneal (i.p.), intravenous (i.v.) or subcutaneous (s.c.)), oral or other routes of administration well known in the art. Parenteral administration is preferred.

The amount used will typically be in the range of about 0.1 mg to about 10 mg/kg of body weight. The antibodies and peptides will preferably be formulated in a unit dosage form.

For example, solid dose forms that can be used for oral administration include capsules, tablets, pills, powders and granules. In such solid dose forms, the active ingredient, i.e., antibody or peptide, is mixed with at least one inert carrier such as sucrose, lactose or starch. Such dose forms can also comprise additional substances other than inert diluents, e.g., lubricating agents, such as magnesium stearate. Furthermore, the dose forms in the case of capsules, tablets and pills may also comprise buffering agents. The tablets, capsules and pills can also contain time-release coatings.

For parenteral administration, one typically includes sterile aqueous or non-aqueous solutions, suspensions or emulsions in association with a pharmaceutically acceptable parenteral vehicle. Examples of non-aqueous solvents or vehicles are propylene glycol, polyethylene glycol, vegetable oils such as olive oil and corn oil, gelatin and injectable organic esters, such as ethyl oleate. These dose forms may also contain adjuvants such as preserving, wetting, emulsifying and dispersing agents. They may be sterilized by, for example, filtration through a bacterial-retaining filter, by incorporating sterilizing agents into the composition, by irradiating the compositions, etc., so long as care is taken not to inactivate the antibody. They can also be manufactured in a medium of sterile water or some other sterile injectable medium before use. Further examples of these vehicles include saline, Ringer's solution, dextrose solution and 5% human serum albumin. Liposomes may also be used as carriers. Additives, such as substances that enhance isotonicity and chemical stability, e.g., buffers and preservatives, may also be used.

The preferred range of active ingredient in such vehicles is in concentrations of about 1 mg/ml to about 10 mg/ml. More preferably, about 3 mg/ml to about 10 mg/ml.

In order to facilitate subsequence cloning of amplified sequences, primers may have restriction enzyme sites appended to their 5' ends. Thus, all nucleotides of the primers are derived from the TAH gene sequences or sequences adjacent thereto except the few nucleotides necessary to form a restriction enzyme site. Such enzymes and sites are well known in the art. The primers themselves can be synthesized using techniques which are well known in the art. Generally, the primers can be made using synthesizing machines which are commercially available.

According to the present invention, a method is also provided for preparing stable cell lines expressing enhanced levels of TAH. The wild-type TAH gene or a part of the gene may be introduced into the cell in a vector operably linked to a promoter that will result in enhanced expression. Such promoters are well known in the art. The vector may be introduced such that the gene remains extrachromosomal. In such a situation, the gene will be expressed by the cell from the extrachromosomal location. Alternatively, the cell may be stably transfected by the vector. Preferably, the gene portion introduced and expressed in the cell carrying the TAH or gene portion should encode a part of the protein which is required for malignant transformation in that cell. More preferred is the situation where the wild-type TAH gene or a part of it is introduced in such a way that it recombines with the chromosome. Such recombination would preferably require stable integration into the cell such as via a double recombination event under the control of a strong promoter which would result in the enhanced expression of the gene. Vectors for introduction of genes both for recombination and for extrachromosomal maintenance are known in the art and any suitable vector may be used. Such a cell can be used in a wide range of activities. For example, one can prepare a drug screen using such a transformed cell line. Thus, one can determine if the compounds tested affect the TAH expressed by the cell. Such a method can be used to select drugs that specifically affect the expression of TAH or as a screen for agents, including known anti-cancer agents, that are effective against TAH-associated tumors. These drugs may be combined with other drugs for their combined or synergistic effects. In contrast, when simply comparing normal cells with neoplastic cells there can be a variety of other factors affecting such cells, thus, such a screen does not provide the same data.

One could also screen for drugs using RuvB⁻ cell lines as a control and then compare the results in cells with TAH protein added. TAH protein can be added to such assays directly or by transforming the cell to express the protein.

These methods of transforming cells to express enhanced levels of TAH may also be able to be used therapeutically, for example, in somatic cell therapy, etc. Such cells can also be used prophylactically to generate an immune response to cells expressing enhanced levels of TAH.

The cell lines stably expressing the TAH gene can also be used for a variety of other purposes including an excellent source of antigen for preparing a range of antibodies using techniques well known in the art as described above.

We have been able to isolate and purify the TAH protein. Preferably, the substantially purified protein has been purified to at least 95%, more preferably the protein is at least 98% pure, still more preferably, the protein is at least 99% pure. We have found that the protein can readily be expressed as a fusion protein, cleaved from the other protein and substantially purified.

Cytotoxic molecules, anti-sense nucleotides, decoys, such as p53-analog molecules containing that portion of p53 which binds to the TAH can be used therapeutically. Alternatively, decoys based upon the present invention can readily be made by using portions of the present proteins. For example, one can prepare a protein portion containing a binding site such as a P53 binding site but which does not contain other functional domains, e.g. helicase activity.

Other compounds that can be used to treat cells overexpressing TAH include compounds that block helicase activity such as CC-1065 [Maine, I. P., et al., *Biochem.* 31:3968–3975 (1992)] and analogs thereof. Compounds that bind to Holliday junctions will also interfere with TAH. Other compounds include those that prevent nucleotide triphosphate (e.g. ATP) activity either by preventing binding to the binding cite such as a decoy or by preventing ATP processing.

The active molecules can be introduced into the cells by microinjection or by liposomes, for example. Alternatively, some such active molecules may be taken up by the cells, actively or by diffusion. Supply of such active molecules will effect an earlier neoplastic state.

Predisposition to cancers can be ascertained by testing normal tissues of humans to obtain base line levels of expression. For example, a person who has a predisposition exhibited by a change in TAH expressing or enhanced levels of expression relative to a baseline level would be prone to develop cancers. This can be determined by testing the protein, DNA or mRNA from any tissue of the person's body. For example, blood can be drawn and the protein, DNA or mRNA extracted from cells of the blood. Alterations of TAH can be detected by any of the means discussed above.

Accordingly, the present invention provides for a wide range of assays (both in vivo and in vitro). These assays can be used to detect cellular activities of TAH, or functional fragments thereof. In these assay systems, TAH, polypeptides, unique fragments, or functional equivalents thereof, may be supplied to the system or produced within the system. For example, such assays could be used to determine whether there is a gene excess or depletion. For example, an in vivo assay systems may be used to study the effects of increased or decreased levels of transcript or polypeptides of the invention in cell or tissue cultures, in whole animals, or in particular cells or tissues within whole animals or tissue culture systems, or over specified time intervals (including during embryogenesis). While excess expressor is typically associated with malignant transformation in non-testicular tissue; any change in level may have consequences, for example, a decrease in expression in the testis.

Classification of nucleotide sequences that are homologous to a TAH gene

Different versions, or "alleles" of the eukaryotic nucleotide sequences of the invention can be classified by their ability to functionally replace an endogenous nucleotide sequence, such as one that is homologous to a TAH gene in normal host testis cell. As used herein, a "wild type" allele is defined as a sequence that can replace an endogenous nucleotide sequence in a normal host cell without having detectable adverse effects on the host cell. A "non-wild type" allele or "alteration" is defined as a eukaryotic nucleotide sequence that cannot replace an endogenous nucleotide sequence in a normal host cell without having detectable adverse effects on the host cell.

An altered alleles of a eukaryotic nucleotide sequence of the invention can differ from wild type alleles in any of several ways including, but not limited to, the amino acid sequence of an encoded polypeptide and the level of expression of an encoded nucleotide transcript or polypeptide product.

Physiological properties that can be monitored include, but are not limited to, growth rate, rate of spontaneous mutation to drug resistance, rate of gene conversion, genomic stability of short repeated DNA sequences, sensitivity or resistance to DNA damage-inducing agents such as UV light, nucleotide analogs, alkylating agents and so on.

Particular "non-wild type" alleles that encode a protein that, when introduced into a host cell, interferes with the endogenous TAH, are termed "dominant negative" alleles.

A large number of vectors have been constructed that contain powerful promoters that generate large amounts of mRNA complementary to cloned sequences of DNA introduced into the vector. For example, and not by way of limitation, expression of eukaryotic nucleotide sequences in *E. coli* may be accomplished using lac, trp, lambda, and recA promoters. See, for example, "Expression in *Escherichia coli*", Section II, pp. 11–195, V. 185, *Methods in Enzymology*, supra; see also Hawley, D. K., and McClure, W. R., "Compilation and Analysis of *Escherichia coli* promoter DNA sequences", *Nucl. Acids Res.*, 11: 4891–4906 (1983), incorporated herein by reference. Expression of eukaryotic nucleotide sequences of the invention, and the polypeptides they encode, in a recombinant bacterial expression system can be readily accomplished.

Yeast cells suitable for expression of the nucleotide sequences of the invention, and the polypeptides they encode, include the many strains of *Saccharomyces cerevisiae* (see above) as well as *Pichia pastoris*. See, "Heterologous Gene Expression in Yeast", Section IV, pp. 231–482, V. 185, *Methods in Enzymology*, supra, incorporated herein by reference. Moreover, a large number of vector-mammalian host systems known in the art may be used. See, Sambrook et al., Volume III, supra and "Expression of Heterologous Genes in Mammalian Cells", Section V, pp. 485–596, V. 185, *Methods in Enzymology*, supra, incorporated herein by reference.

Suitable expression systems include those that transiently or stably expressed DNA and those that involve viral expression vectors derived from simian virus 40 (SV 40), retroviruses, and baculoviruses. These vectors usually supply a promoter and other elements such as enhancers, splice acceptor and/or donor sequences, and polyadenylation signals. Possible vectors include, but are not limited to, cosmids, plasmids or modified viruses, but the vector system must be compatible with the host cell used. Viral vectors include, but are not limited to, vaccinia virus, or lambda derivatives. Plasmids include, but are not limited to, pBR322, pUC, or Bluescript® (Stratagene) plasmid derivatives. Recombinant molecules can be introduced into host cells via transformation, transfection, infection, electroporation, etc. Generally, expression of a protein in a host is accomplished using a vector containing DNA encoding that protein under the control of regulatory regions that function in the host cell.

In particular, expression systems that provide for overproduction of TAH can be prepared using, for example, the methods described in U.S. Pat. No. 4,820,642 (Edman et al., Apr. 11, 1989), incorporated herein by reference. The general requirements for preparing one form of expression vector capable of overexpression are: (1) the presence of a gene (e.g., a prokaryotic gene) into which a nucleotide sequence capable of encoding TAH can be inserted; (2) the promoter of this prokaryotic gene; and (3) a second promoter located upstream from the prokaryotic gene promoter which overrides the prokaryotic gene promoter, resulting in overproduction of the extracellular matrix protein. The second promoter is obtained in any suitable manner. Possible host cells into which recombinant vectors containing the nucleotide sequences of the invention can be introduced include, for example, bacterial cells, yeast cells, non-human mammalian cells in tissue culture or in situ, and human cells in tissue culture but not in situ.

Nucleotide sequences of the invention that have been introduced into host cells can exist as extra-chromosomal sequences or can be integrated into the genome of the host cell by homologous recombination, viral integration, or other means. Standard techniques such as Northern blots and Western blots can be used to determine that introduced sequences are in fact being expressed in the host cells.

Host cells carrying such introduced sequences can be analyzed to determine the effects that sequence introduction has on the host cells. In particular, cells could be assayed for alterations in the rate of accumulation of spontaneous mutations (e.g. by the rate of spontaneous mutation to drug resistance), in the rate of reversion of mutations, in the frequency of homologous recombination, in the frequency of recombination between divergent sequences, or in the genomic stability of short repeated sequences. In particular, mammalian cells carrying introduced sequences of the invention could be tested for p53 binding or for sensitivity to agents that induce DNA damage such as UV-light, nucleotide analogs, alkylating agents, etc.

In particular embodiments, a nucleotide sequence of the invention may be used to overexpress an endogenous gene by homologous recombination, and thereby create a turned-on TAH non-testicular cell, tissue, or animal. For example, and not by way of limitation, a recombinant human nucleotide sequence of the present invention may be engineered to overexpress the TAH gene by the methods described above. Such a construct, under the control of a suitable promoter operatively linked to a nucleotide sequence of the invention, may be introduced into a cell by a technique such as transformation, transfection, transduction, injection, etc. In particular, transformed stem cells may generate transgenic animals the TAH gene and the polypeptide it encodes, via germ line transmission.

In another embodiment, a construct can be provided that, upon transcription, produces an "anti-sense" nucleic acid sequence which, upon translation, will not produce the required TAH polypeptide.

A "transgenic animal" is an animal having cells that contain DNA which has been artificially inserted into a cell, which DNA becomes part of the genome of the animal that develops from that cell. The preferred DNA contains human TAH nucleotide sequences and may be entirely foreign to the transgenic animal, but which is inserted into the animal's genome at a location which differs from that of the natural copy. Transgenic animals could provide good model systems for studying the development of cancer, the effects of potential therapeutic reagents, and the carcinogenicity of chemical agents administered to the animals.

Functionally equivalent substitutes for an amino acid within the sequence may be selected from other members of the class to which the amino acid belongs. The non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Substantial changes in functional or, for example, immunological properties may be avoided by selecting substitutes that do not differ from the original amino acid residue. More significantly, the substitutions can be chosen for their effect on: (i) maintaining the structure of the peptide backbone in the area of the substitution, for example, as a sheet or helical conformation; (ii) maintaining the charge or hydrophobicity of the molecule at the target side; or (iii) maintaining the bulk of the side chain. The substitutions that in general could expected to induce greater changes, and therefore should be avoided, are those in which: (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl, or (e) a residue having a bulky side chain, e.g., phenylalanine, is substituted for one (or by) one not having such a side chain, e.g., glycine.

The functional equivalence of two polypeptide sequences can be assessed by examining physical characteristics (e.g. homology to a reference sequence, the presence of unique amino and sequences, etc.) and/or functional characteristics analyzed in vitro or in vivo.

Functional equivalents of wild type TAH and functional fragments thereof are thus included herein.

Also included within the scope of the invention are polypeptides or unique fragments or derivatives thereof that are differentially modified during or after translation, e.g., by phosphorylation, glycosylation, crosslinking, acylation, proteolytic cleavage, linkage to an antibody molecule, membrane molecule or other ligand, (Ferguson, et al., *Ann. Rev. Biochem.* 57:285–320, 1988).

Polypeptide fragments of the invention can be produced, for example, by expressing cloned nucleotide sequences of the invention encoding partial polypeptide sequences. Alternatively, polypeptide fragments of the invention can be generated directly from intact polypeptides. Polypeptides can be specifically cleaved by proteolytic enzymes, including, but not limited to, trypsin, chymotrypsin or pepsin. Each of these enzymes is specific for the type of peptide bond it attacks. Trypsin catalyzes the hydrolysis of peptide bonds whose carbonyl group is from a basic amino acid, usually arginine or lysine. Pepsin and chymotrypsin catalyze the hydrolysis of peptide bonds from aromatic amino acids, particularly tryptophan, tyrosine and phenylalanine. Alternate sets of cleaved polypeptide fragments are generated by preventing cleavage at a site which is susceptible to a proteolytic enzyme. For example, reaction of the ε-amino groups of lysine with ethyltrifluorothioacetate in mildly basic solution yields a blocked amino acid residue whose adjacent peptide bond is no longer susceptible to hydrolysis by trypsin. Goldberger et al. Biochem., 1:401 (1962). Treatment of such a polypeptide with trypsin thus cleaves only at the arginyl residues.

Polypeptides also can be modified to create peptide linkages that are susceptible to proteolytic enzyme catalyzed hydrolysis. For example, alkylation of cysteine residues with β-halo ethylamines yields peptide linkages that are hydrolyzed by trypsin. Lindley, Nature, 178: 647 (1956). In addition, chemical reagents that cleave polypeptide chains at specific residues can be used. Withcop, Adv. Protein Chem. 16: 221 (1961). For example, cyanogen bromide cleaves polypeptides at methionine residues. Gross & Witkip, J. Am Chem Soc., 83: 1510 (1961). Thus, by treating TAH or fragments thereof with various combinations of modifiers, proteolytic enzymes and/or chemical reagents, numerous discrete overlapping peptides of varying sizes are generated. These peptide fragments can be isolated and purified from such digests by chromatographic methods.

Alternatively, polypeptides of the present invention can be synthesized using an appropriate solid state synthetic procedure. Steward and Young, *Solid Phase Peptide Synthesis*, Freemantle, San Francisco, Calif. (1968). A preferred method is the Merrifield process. Merrifield, *Recent Progress in Hormone Res.,* 23: 451 (1967). The activity of these peptide fragments may conveniently be tested using, for example, a filter binding or immunologic assay as described herein.

Also within the scope of the invention are nucleic acid sequences or proteins encoded by nucleic acid sequences derived from the same gene but lacking one or more structural features as a result of alternative splicing of transcripts from a gene that encodes TAH.

Nucleic acid sequences complementary to DNA or RNA sequences encoding polypeptides of the invention or a functionally active portion(s) thereof are also provided. In animals, particularly transgenic animals, RNA transcripts of a desired gene or genes may be translated into polypeptide products having a host of phenotypic actions. In a particular aspect of the invention, antisense oligonucleotides can be synthesized. These oligonucleotides may have activity in their own right, such as antisense reagents which block translation or inhibit RNA function. Thus, where human polypeptide is to be produced utilizing the nucleotide sequences of this invention, the DNA sequence can be in an inverted orientation which gives rise to a negative sense ("antisense") RNA on transcription. This antisense RNA is not capable of being translated to the desired product, as it is in the wrong orientation and would give a nonsensical product if translated.

A preferred oligonucleotide probe typically has a sequence somewhat longer than that used for the PCR primers. A longer sequence is preferable for the probe, and it is valuable to minimize codon degeneracy. A representative protocol for the preparation of an oligonucleotide probe for screening a cDNA library is described in Sambrook, J. et al., Molecular Cloning, Cold Spring Harbor Press, New York, 1989. In general, the probe is labelled, e.g., $^{32}P$, and used to screen clones of a cDNA or genomic library.

Preferred nucleotide probes are at least 20–30 nucleotides long, and contain at least 15–20 nucleotides that are complimentary to their target sequence in a TAH gene. Preferred nucleotide probes can be radioactively labelled or conjugated to fluorescent tags such as those available from New England Biolabs (Beverly, Mass.) or Amersham (Arlington Heights, Ill.) and can be used to probe, for example, Southern blots, Northern blots, plaque lifts, colony lifts, etc. Nucleotide probes of the invention include, for example, probes made by chemical synthesis and probes generated by PCR.

Preferred nucleotide probes of the invention, be they oligonucleotides, PCR—generated fragments, or other nucleic acid sequences (e.g. isolated clones), can be used in the general protocol described above.

The full-length cDNA sequence of TAH is shown in FIGS. 4A–4D. The deduced amino acid sequence consists of 670 residues with a predicted molecular mass of 75,000 Dalton. It has two putative nuclear localization signals as indicated. Some predicted structural features of this protein are also included in FIGS. 4A–4D. Phosphorylation sites for protein kinase C, and helicase motif I (NTP-binding site), II, IV and V are also indicated in FIGS. 4A–4D.

Sequence analysis and a search of the GenBank database revealed that TAH shares significant homology with a number of helicases, especially RuvB and SV40 T-antigen (FIGS. 5 and 6), and contains hallmarks of this family of proteins including helicase motifs I (ATP-binding motif), II, IV and V. Of interest, there is a consensus phosphorylation site for protein kinase C in the putative ATP-binding site of TAH.

The present invention is further illustrated by the following examples. These examples are provided to aid in the understanding of the invention and are not construed as a limitation thereof.

EXAMPLE 1

Identification and Isolation of TAH Gene by Palindromic cDNA Display

A powerful method termed Palindromic PCR cDNA display modified from Liang and Pardee's original procedure was employed to search for DNA repair genes differentially expressed in both human normal testis and tumor tissue. The first cDNA fragment of TAH was identified and isolated by this method. Briefly, paired mRNAs (100 ng/each) of colon tumor tissue (T) and the adjacent normal colon tissue (N) from the same patient were reverse transcribed to cDNAs with the primer 5'-TCCTTAGAAC, followed by 40 cycles of palindromic PCR using the same primer. Amplified cDNA fragments ($^{35}S$-labeled) were resolved on a polyacrylamide gel. cDNA patterns derived from tumor tissue and the adjacent normal tissue were directly compared and differential cDNA bands were detected. FIG. 1 shows a cDNA band (TAH) overexpressed in the tumor tissue. This cDNA band was excised and recovered from the gel for reamplification. Reamplified TAH cDNA fragment was cloned and used to screen a cDNA library for the full length sequence of TAH cDNA.

EXAMPLE 2

Nucleotide and Deduced Amino Acid Sequence of Full-length TAH

The first TAH cDNA fragment was used as a probe to screen a human cDNA library until a full open reading frame was obtained. The open reading frame of TAH encodes a 670 amino acid sequence with molecular weight of 75 kD (FIGS. 4A–4D). TAH protein contains a typical ATP or GTP binding sites and two putative nuclear localization signals (NLS). A cAMP phosphorylation site, 11 protein kinase C (PKC) phosphorylation sites and 19 casein kinase 11 phosphorylation sites are all indicated in FIGS. 4A–4D.

Plasmid (p bluescript vector) encoding TAH (TAH/PBS) can readily be used to construct an expression vector by known means, for example, cleaving with appropriate restriction enzymes according to manufacturers directions and inserting the TAH cDNA into an appropriate vector such as a PGEX-2T vector. This expression vector can be used to transform a cell and to express the TAH protein. See, Sambrook, J. et al., *Molecular Cloning*, Cold Spring Harbor Press, New York, 1989.

EXAMPLE 3

Homology between TAH and RuvB, SV40 T Antigen and other Helicase

RuvB is a well known DNA helicase involved in DNA recombination repair in *E. coli*. A database search revealed that TAH shares significant homology with RuvB. TAH and RuvB share 21% identity and 40% conservation in 238 amino acid sequence (FIG. 5). Highly homology between TAH and RuvB suggested their functional similarity.

SV40 Tumor antigen is a very important protein related to cell oncogenetic transformation. This protein has DNA helicase and RNA helicase activities and contains P53 and RB binding domains. TAH also shares significant homology with SV40 T antigen. TAH and SV40 T antigen share 21% identity and 30% conservation in 210 amino acid sequence (FIG. 6). The P53 binding site in the SV40 T antigen is located in this homologous domain.

EXAMPLE 4

Analysis of Purified GST-TAH and TAH Protein

Figure 16:
FIG. 16 is a SDS-PAGE of purified GST-TAH and TAH proteins.

Full-length TAH cDNA was inserted into a PGEX-2T vector. TAH was overexpressed as a fusion protein with glutathione transferase (GST) in E. coli and purified by binding to glutathione-conjugated beads. TAH was released from GST-beads by treatment with thrombin while the TAH-GST fusion protein was eluted by excess glutathione. Purified GST-TAH and TAH protein was denatured, resolved by 8% polyacrylamide gel, and stained with Coomassie blue (FIG. 16).

Figure 22:
FIG. 22 is a Western blot analysis of purified GST-TAH fusion protein and TAH protein.

Purified TAH protein was used to immunize mice for the production of monoclonal antibodies. One clone of monoclonal antibodies was designated HT-1 which can recognize both denatured and native TAH protein. FIG. 22 showed Western blot analysis of purified GST-TAH and TAH protein. The blot was immunoprobed with an anti-TAH monoclonal antibody HT-1 and visualized with an ECL detection kit.

EXAMPLE 5

Helicase Activity of TAH Protein

We tested whether TAH has DNA-binding and helicase activity. For example, RuvB requires RuvA for efficient DNA-binding and helicase activity. As a complex, RuvAB have ATP-dependent helicase activity and promotes branch migration of Holliday junction by DNA unwinding. Similar to RuvB, purified TAH-GST or TAH did not exhibit significant helicase activity using an M13 single stranded DNA containing a partial duplex as a substrate. However, when TAH-GST was captured on glutathione beads, incubated with tumor cell extracts, washed, and then eluted with glutathione, the complex has unambiguous ATP-dependent helicase activity. This activity is specifically inhibited by the anti-TAH mAb HT-1. Similar to RuvA, the accessory molecule(s) required for TAH's helicase activity is not present in normal fibroblast cells, but are detected after UV irradiation. Like RuvA and RuvB, both TAH and the accessory component(s) are believed to be induced by UV light concomitantly. The accessary activity is also present in human carcinoma cell lines including Clone A, a poorly differentiated human colon carcinoma cell line.

Figure 9:
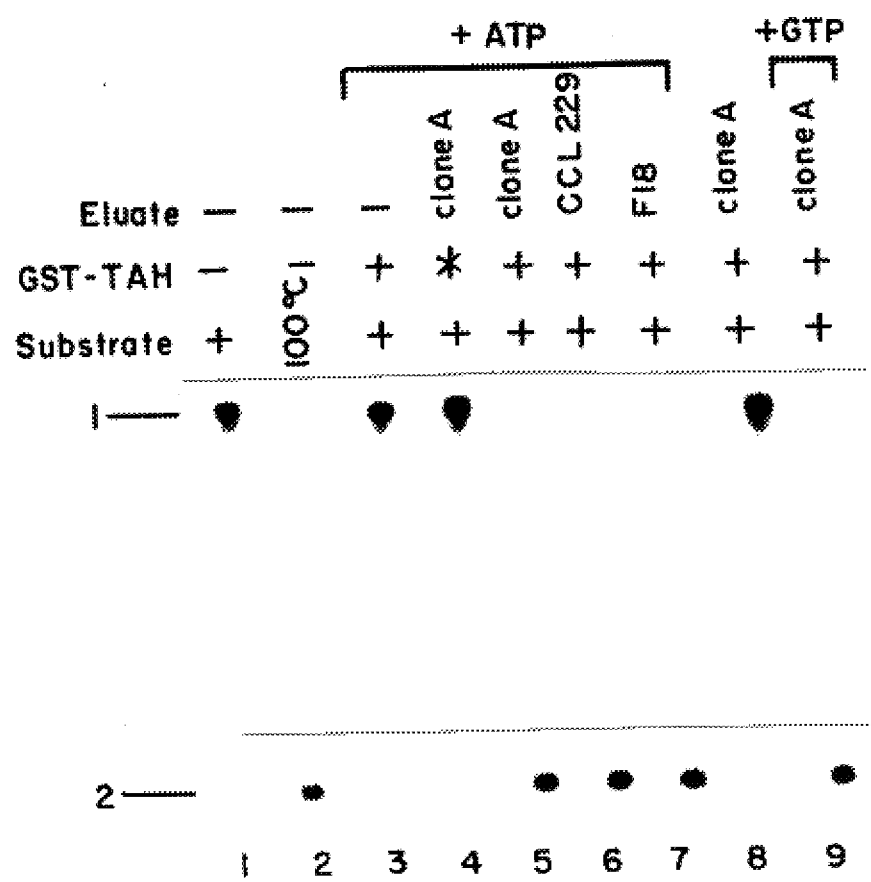
FIG. 9 shows activity of the TAH protein.

In the experiment depicted in FIG. 9, all reaction mixtures contained 1 μM DNA substrate (single strand M13 DNA annealed with a $^{32}$P-labeled 70 nt fragment) in helicase buffer with 2 mM ATP (lane 3–7), or without ATP (lane 8), or with 2 mM GTP (lane 9). For reaction of lane 3, 200 nM of purified GST-TAH fusion protein was added. For reactions of lane 4–9, purified GST-TAH protein (lane 5–9) or GST protein (lane 4) bound on glutathione-conjugated beads were incubated with nuclear extracts from cloneA (lane 4, 5, 8, 9) or CCL229 (lane 6) or F18 (lane 8), followed by several washes, and then eluted with glutathione, the complex was added to the reaction mixtures. Reactions were incubated at 37° C. for 30 minutes and stoped, products were analysized by gel electrophoresis. Lane 1, showing $^{32}$P-labeled DNA substrate. Lane 2, showing heat-denatured substrate for control.

Figure 10:
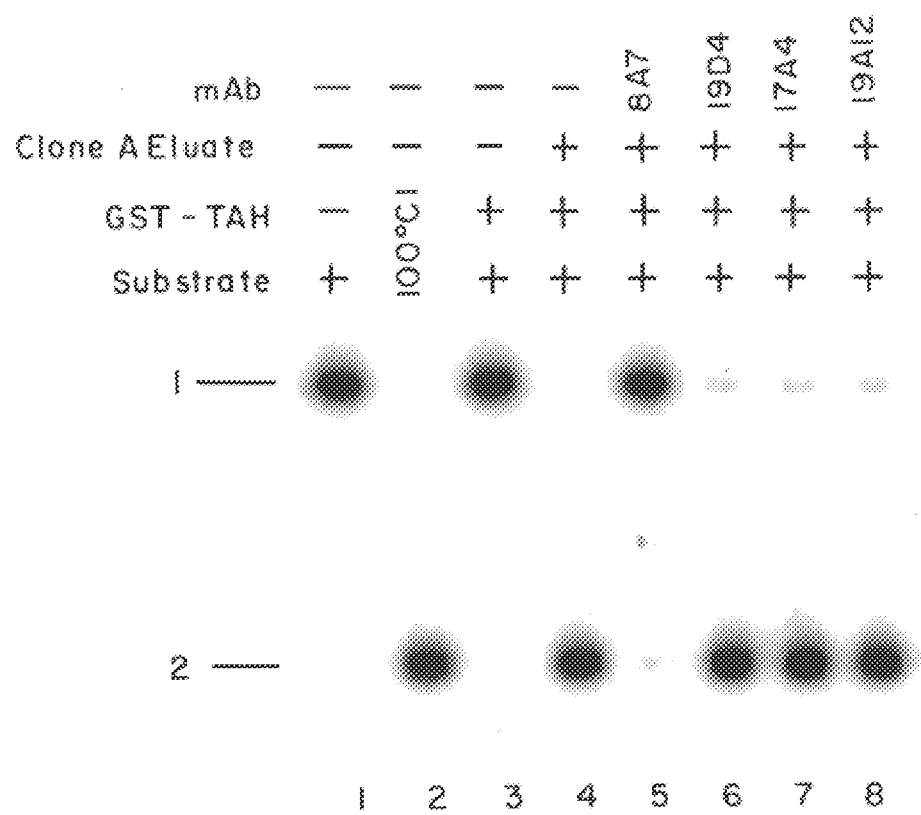
FIG. 10 shows that TAH helicase activity affected by anti-TAH monoclonal antibody.

TAH helicase activity was inhibited by anti-TAH monoclonal antibody. FIG. 10 shows that TAH helicase activity affected by anti-TAH monoclonal antibody. Reaction mixture contained 1 μM DNA substrate (single strand M13 DNA annealed with a $^{32}$P-labeled 70 nt fragment) in helicase buffer with 2 mM ATP (lane 3–8). For reaction of lane 3, 200 nM of purified GST-TAH fusion protein was added. For reactions of lane 4–8, purified GST-TAH protein bound on glutathione-conjugated beads were incubated with nuclear extracts from clone A, followed by several washes, and then eluted with glutathione, the complex was used for assay. For reactions of lane 5–8, the complex was incubated with anti-TAH monoclonal antibodies as indicated, and then added to reaction mixtures. Reactions were incubated at 37° C. for 30 minutes and stoped, products were analysized by gel electrophoresis. Lane 1, showing $^{32}$P-labeled DNA substrate. Lane 2, showing heat-denatured substrate for control.

EXAMPLE 6

P53-binding activity of TAH

We tested whether TAH also binds p53. Our tests show that TAH binds to p53.

Figure 11:
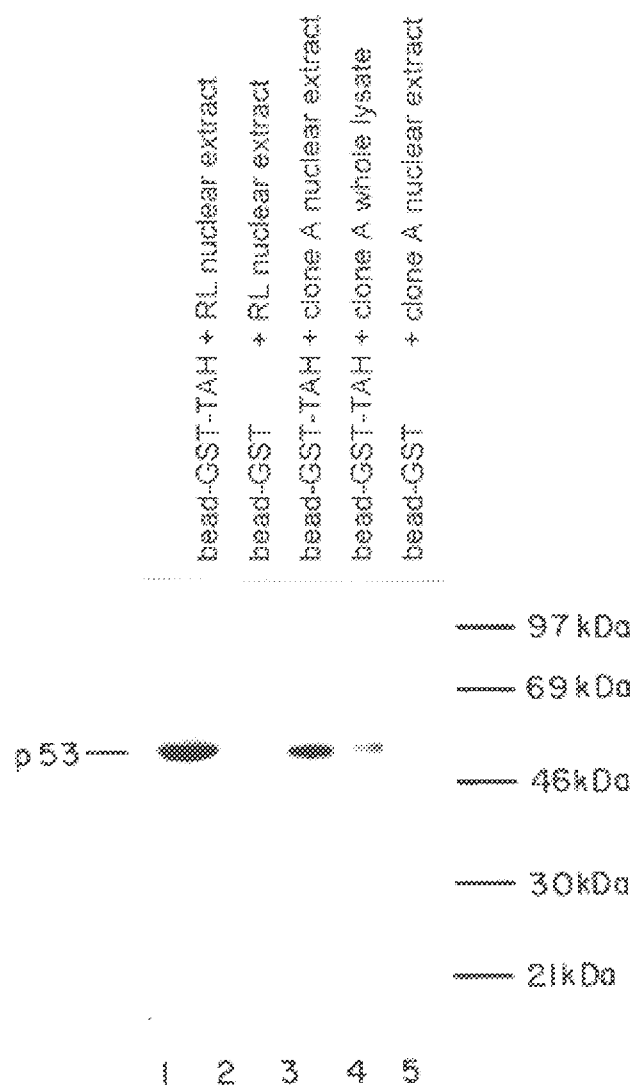
FIG. 11 illustrates the P53 binding activity of TAH.

Purified GST-TAH protein (FIG. 11, lanes 1, 3, 4) or GST protein (lanes 2 and 5) bound to glutathione-conjugated beads were incubated with the same amount of nuclear extracts from RL cells (lane 1 and 2) and Clone A cells (lanes 3 and 5) or whole cell lysate of Clone A (lane 4), followed by three washes. Eluted proteins were blotted with anti-P53 mAb (BP53-12 from Sigma). The antibody was visualized with an ECL detection kit (Amersham).

EXAMPLE 7

Wild Type P53 Inhibited TAH Helicase Activity

Figure 17:
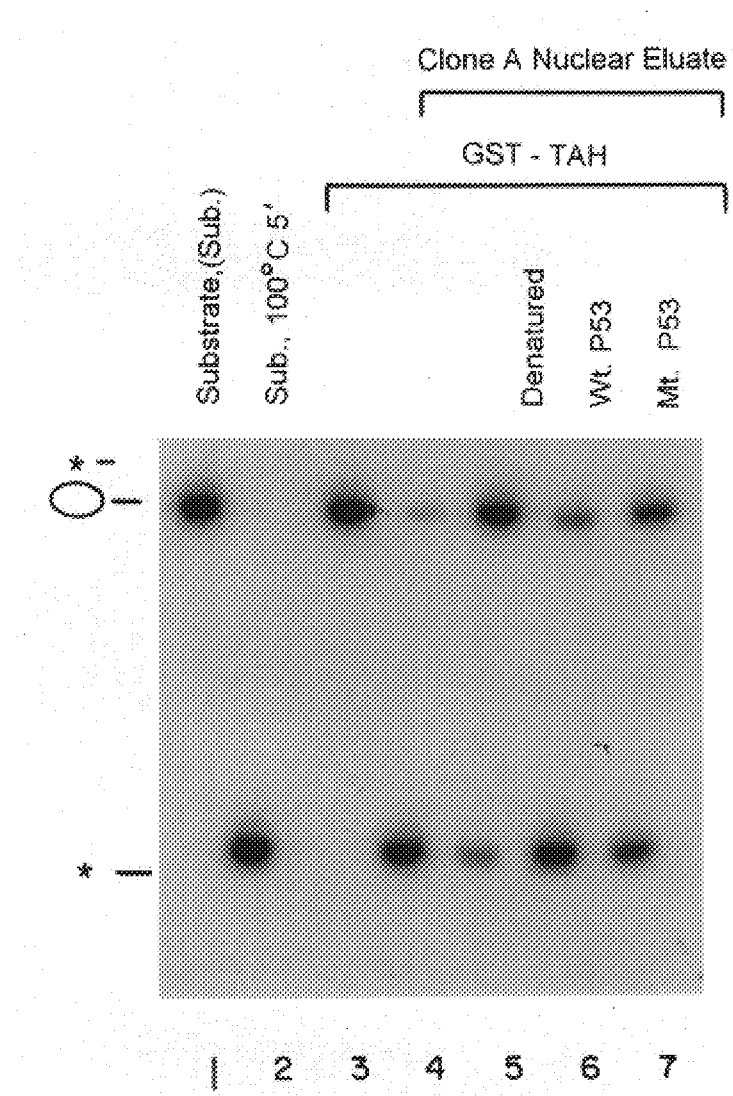
FIG. 17 shows the inhibition of TAH helicase activity by wild-type P53.

We tested wild type p53 for TAH helicase inhibition activity. Our test show that the inhibition of TAH helicase activity by wild-type P53 (FIG. 17). Reaction mixture contained 1 μM DNA substrate (single strand M13 DNA annealed with a $^{32}$P-labeled 70 nt fragment) in helicase buffer with 2 mM ATP. For reaction of lane 3, 200 nM of purified GST-TAH fusion protein was added. For reactions of lane 4–7, purified GST-TAH protein bound on glutathione-conjugated beads were incubated with nuclear extracts from clone A, followed by several washes, and then eluted with glutathione, the complex was used for assay. For reactions of lane 5, the complex was heated before incubated with substrate. For reactions of lane 5, the complex was heated before incubated with substrate. For reactions of lane 6 and 7, the complex was incubated with 300 nM of wild type P53 or mutated P53 before incubated with DNA substrate. Reactions were incubated at 37° C. for 30 minutes and stopped, products were analyzed by gel electrophoresis. Lane 1, shows heat-denatured substrate for control.

Figure 18:
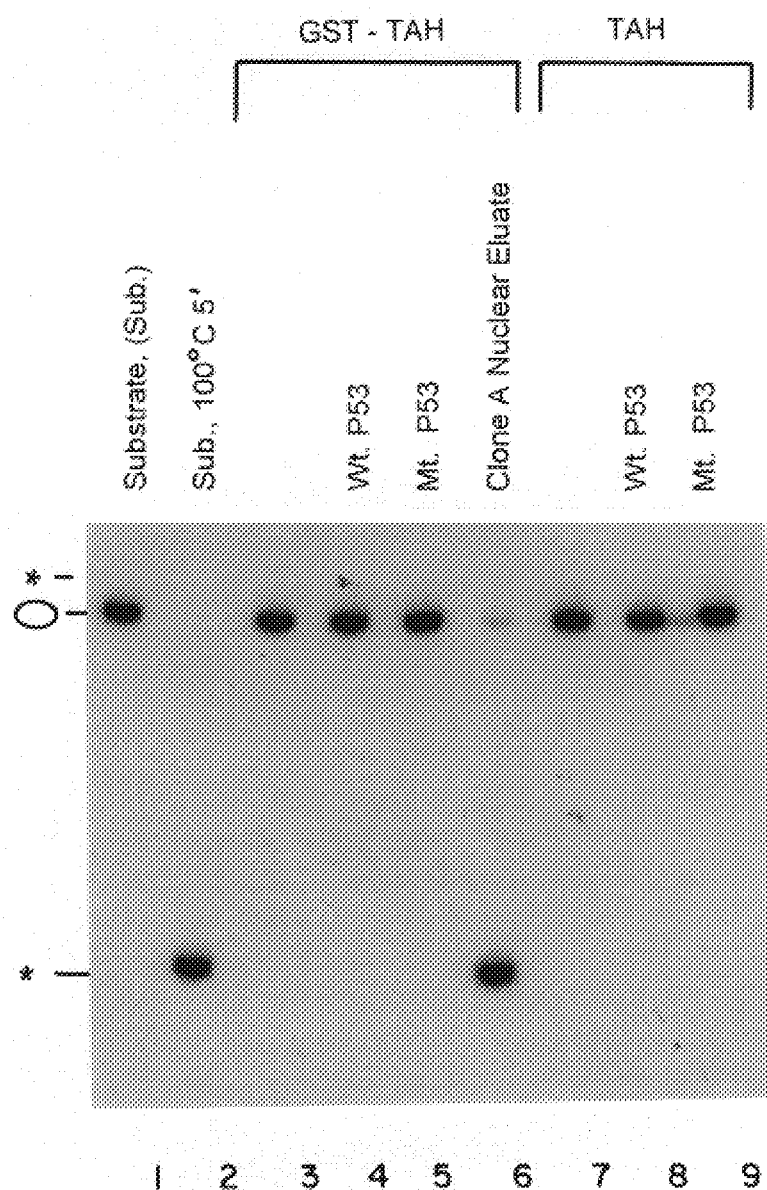
FIG. 18 demonstrates P53 is not human "RuvA" equivalent.

The experiment depicted in FIG. 18 demonstrates P53 is not a human "RuvA"equivalent. Reaction mixture contained 1 μM DNA substrate (single strand M13 DNA annealed with a $^{32}$P-labeled 70 nt fragment) in helicase buffer with 2 mM ATP. Lane 3, 200 nM of purified GST-TAH fusion protein was added. Lane 4, 200 nM of purified GST-TAH fusion protein and wild type P53 were added. Lane 5, 200 nM of purified GST-TAH fusion protein and mutated P53 were added. Lane 6, purified GST-TAH protein bound on glutathione-conjugated beads were incubated with nuclear extracts from clone A, followed by several washes, and then eluted with glutathione, the complex was added and showed helicase activity. Lane 7, 200 nM of purified TAH protein was added. Lane 8, 200 nM of purified TAH protein and wild type P53 were added. Lane 9, 200 nM of purified TAH protein and wild type P53 were added. Lane 9, 200 nM of purified TAH protein and mutated P53 were added. Reactions were incubated at 37° C. for 30 minutes and stoped, products were analysized by gel electrophoresis. Both wild type P53 and mutated P53 did not replace nuclear eluate to help TAH or GST-TAH helicase activity. Lane 1, shows $^{32}$P-labeled DNA substrate. Lane 2, shows heat-denatured substrate for control.

EXAMPLE 8

Induction of TAH by UV Irradiation

TAH Enhanced UV resistance

In view of the sequence similarities that TAH shares with RuvB and SV40 T-antigen, the following experiments were performed. They show functional similarities between TAH and other helicases.

We tested whether TAH is inducible by UV irradiation. Immunofluorescent stainings show that TAH is dramatically induced in a normal human diploid fibroblast strain, exposed to UV light. TAH was detected in nuclei as early as 45 min after irradiation. Clearly TAH shares UV-inducibility with RuvB.

Figure 8A:
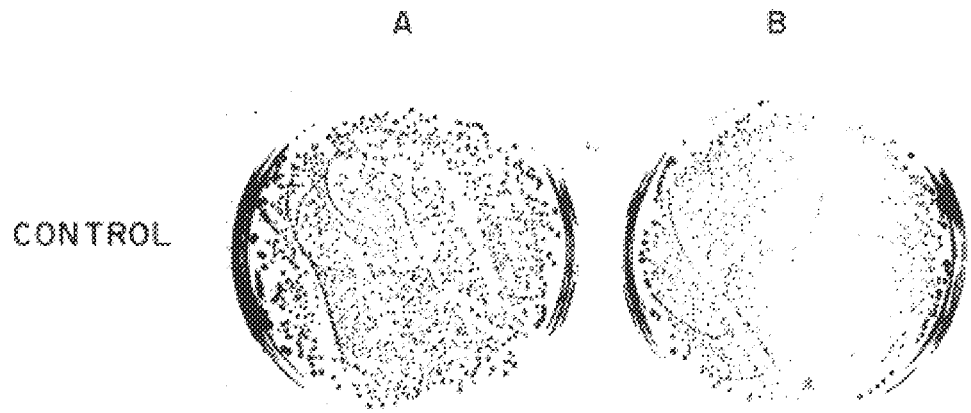
FIG. 8 illustrates increased UV resistance of bacteria E. coli transformed with TAH gene.
Figure 8B:
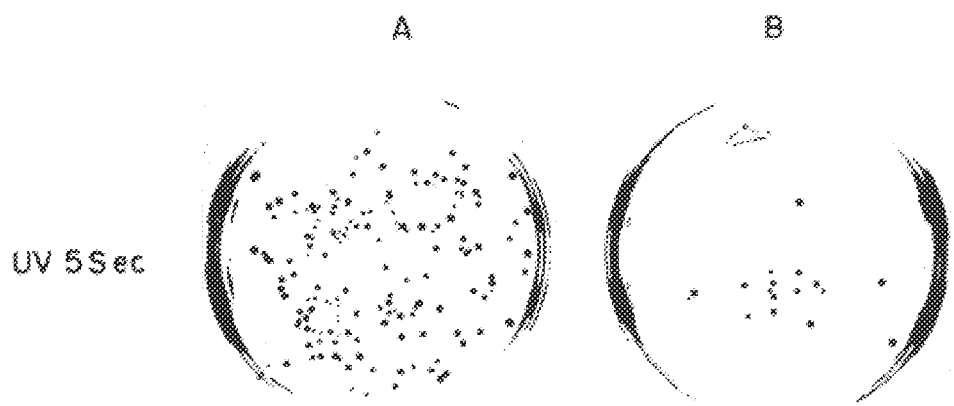
Figure 8C:
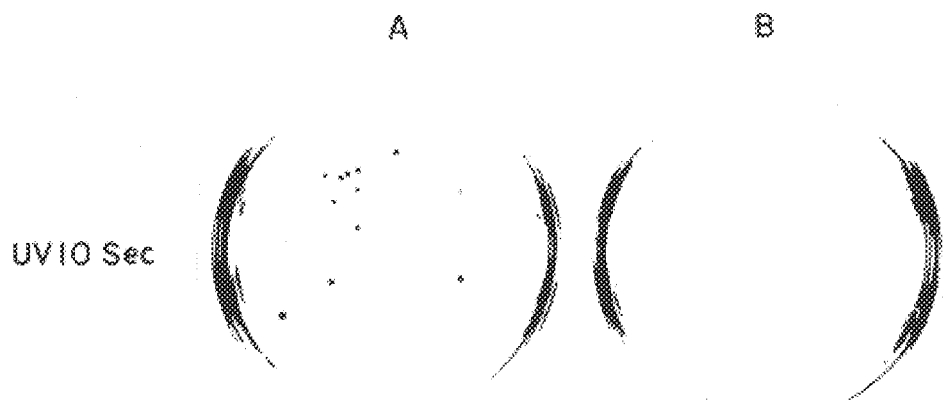

We tested whether an overexpression of TAH could confer cells with increased resistance to UV irradiation was explored. E. coli DH5a were transformed with TAH/PGEX2T (A) or PGEX2T (B). The transformed cells were then cultured, E. coli cells were cultured, induced with IPTG at 37° C. for 3.5 hours, plated on LB agar (100 ug of Ampicillin/ml) with the same number of cells, exposed to UV light for 5 sec or 10 sec, and then incubated at 37° C. for 16 hr. Control plates were not exposed to UV light. FIG. 8 demonstrates that a significant increase in UV-resistance was detected in E. coli when TAH-GST expression was induced by IPTG.

Figure 15A:
FIGS. 15A and B show the induction of TAH by UV irradiation.
Figure 15B:
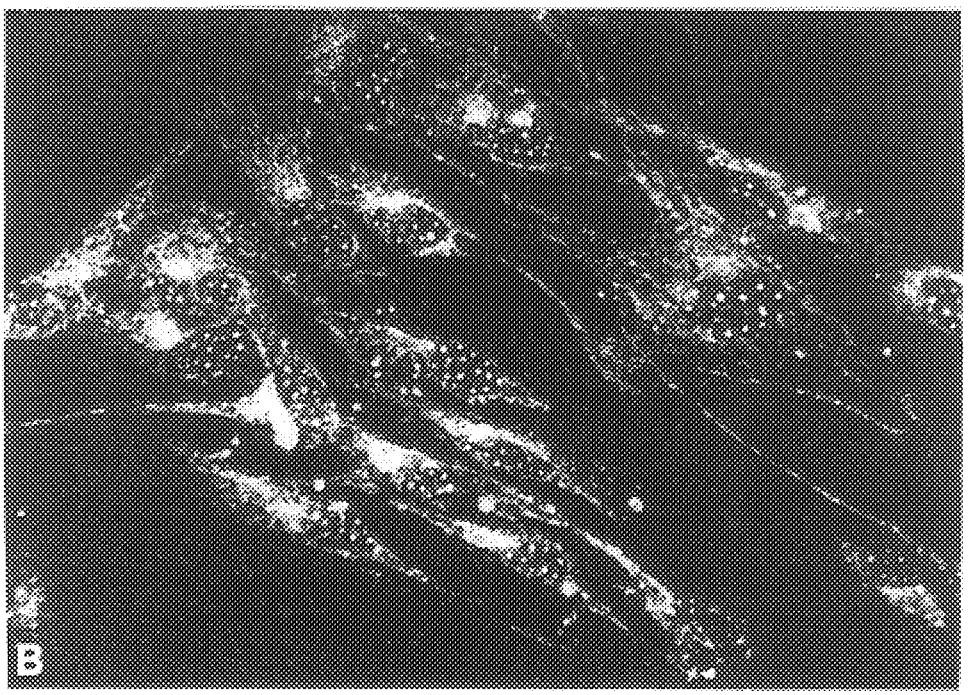

FIG. 15 shows the induction of TAH by UV irradiation. Immunofluorescent staining showed that TAH protein is dramatically induced in human normal fibroblasts MRC-5 by exposure to UV light (50 J/m$^2$) followed by 2 hours recovery. A, control (without UV exposure), B, UV induction.

FIG. 23 illustrates that high level of TAH protein are related to resistance to γ-irradiation. F18 cell containing very high level TAH protein was from adenovirus transformed Rat1 cell. Normal Rat1 cell has little TAH protein. A, control showing same number of cells of Rat1 and F18 were seeded. B, after γ-irradiation (2000 rads for 1.5 min) Rat1 and F18 cells were recovered for 4 days and then stained. F18 cells showed much more resistant to γ-irradiation than Rat1 cells.

EXAMPLE 9

Human "RuvA" Equivalent is also UV Inducible

Figure 19:
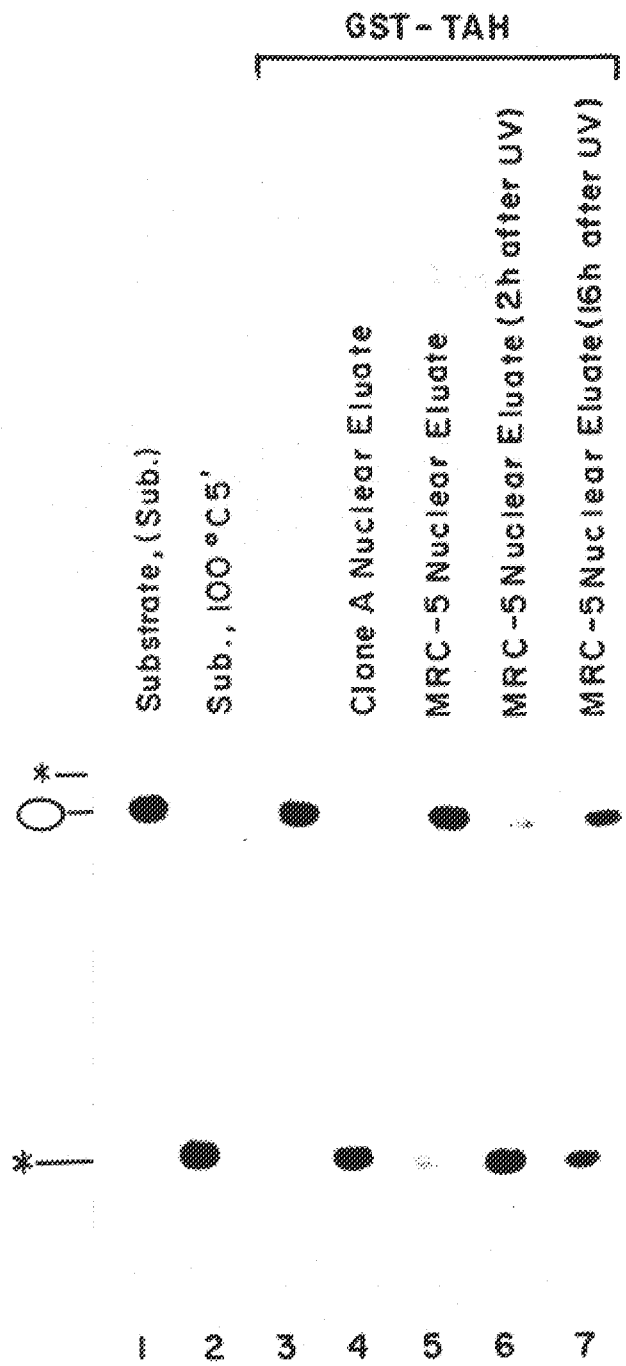
FIG. 19 shows that human "RuvA" equivalent is also UV inducible.

The results of the experiment depicted in FIG. 19 show that there is present in these cells a human "RuvA" equivalent that is also UV inducible. Reaction mixture contained 1 μM DNA substrate (single strand M13 DNA annealed with a $^{32}$P-labeled 70 nt fragment) in helicase buffer with 2 mM ATP. Lane 3, 200 nM of purified GST-Tah fusion protein was added. Lane 4–7, purified GST-TAH protein bound on glutathione-conjugated beads were incubated with nuclear extracts from clone A cells (lane 4) or normal MRC-5 cells (lane 5) or MRC-5 cells exposed to UV followed by 2 hours recovery (lane 6) and 16 hours recovery (lane 7), followed by several washes, and then eluted with glutathione, the complex was added to the reaction mixtures. Reactions were incubated at 37° C. for 30 minutes and stoped, products were analysized by gel electrophoresis. Lane 1, shows heat-denatured substrate for control. GST-TAH combined with nuclear eluate from the MRC-5 cell 2 hours after UV exposure showed a great helicase activity (lane 6), but GST-TAH combined with nuclear eluate from the MRC-5 cell 16 hours after UV exposure showed a less helicase activity (lane 7).

EXAMPLE 10

TAH Dissociated Holliday Junction

Figure 20:
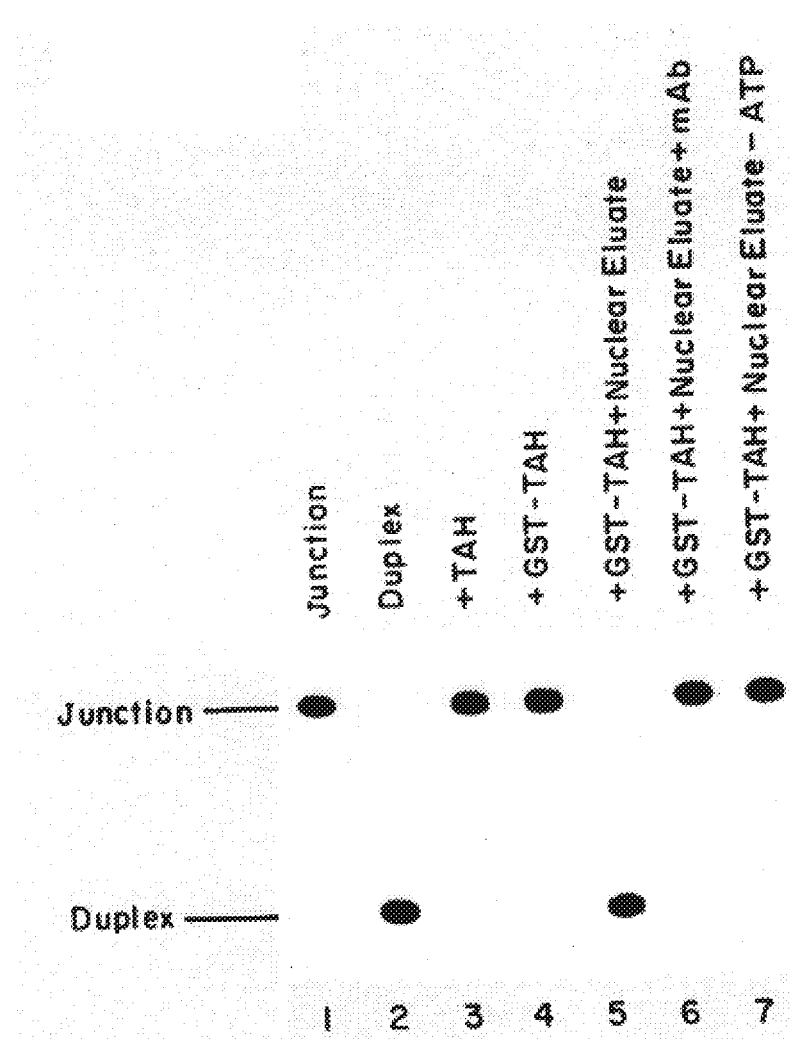
FIG. 20 illustrates the dissociation of synthetic Holliday junction by TAH protein.

The experiment depicted in FIG. 20 illustrates the dissociation of synthetic Holliday junction by TAH protein. The reaction mixture contained 0.5 uM $^{32}$P-labeled synthetic Holliday junction DNA in a reaction buffer containing 50 mM Tris-Cl (pH 8.0), 10 mM MgCl$_2$, 50 mM KCl, 2 mM ATP, 1 mM DTT, 100 ug of BSA per ml were incubated for 15 min at 37° C. Lane 3 and 4, 200 nM of TAH or GST-TAH proteins were present. Lanes 5–7, purified GST-TAH protein bound on glutathione-conjugated beads were incubated with nuclear extracts from clone A, followed by several washes, and then eluted with glutathione, the complex was used for assay. Lane 5, shows dissociation of the junction by GST-TAH protein with nuclear eluate. Lane 6, the complex was incubated with a anti-TAH antibody before reaction, the antibody blocked dissociation of the junction by GST-TAH protein with eluate. Lane 7, ATP was absent in the reaction, without ATP the junction was not dissociated by GST-TAH protein with nuclear eluate. Lane 1 is $^{32}$P-labeled junction and lane 2 is $^{32}$P-labeled duplex.

EXAMPLE 11

TAH Protein Structure Revealed by Electron Microscopy

FIG. 13 shows TAH protein structure revealed by electron microsopy. Negative-stained TAH shows a hexamer-based donut shape, could be a quadruple-hexamer. A, top view; B, side view.

EXAMPLE 12

Overexpression of TAH in Testis Tissue

Figures 12A, 12B:
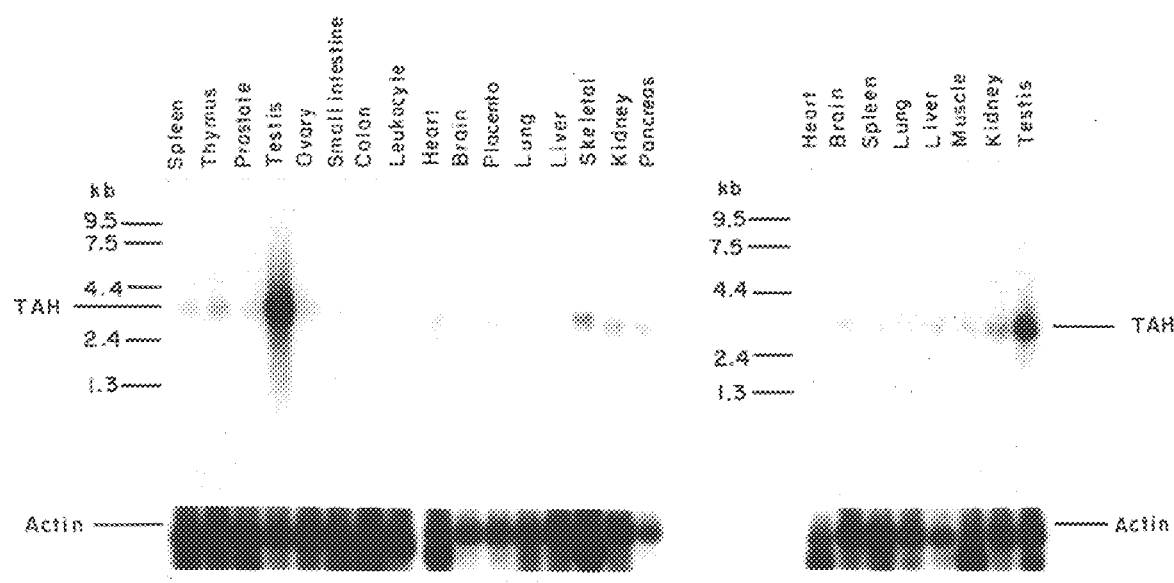
FIGS. 12A and B are Northern blot analysis of TAH mRNA expression in human tissues (A) and mouse tissues (B).
Figure 14A:
FIGS. 14A–D illustrate immunofluorescent staining of TAH in cultured cells. TAH protein is seen in nuclei of most cancer cells and several virus transformed cells. Clone A (D) and MIP101 (C), human colon carcinoma; MRC-5 (B) and 3T3 (A), human and mouse normal fibroblasts.
Figure 14B:
Figure 14C:
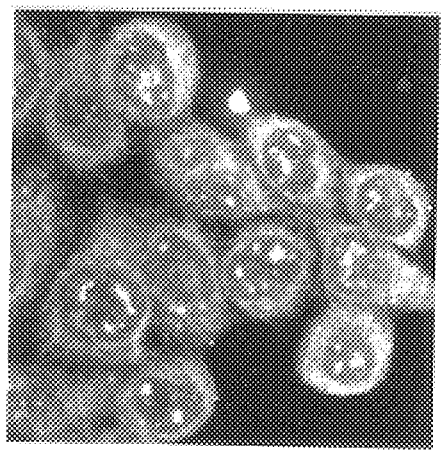
Figure 14D:
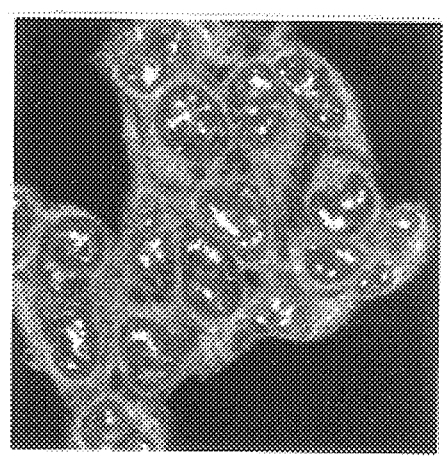

Northern blot analysis of TAH mRNA expression in human tissues (A) and mouse tissues (B) was performed. The results are illustrated in FIG. 12. RNA from various tissues as indicated were probed with a $^{32}$P-labeled TAH cDNA (top panel) and probed with a $^{32}$P-labeled cDNA encoding actin. TAH mRNA is overexpressed in testis from both human and mouse. Other tissue express little TAH and mRNA.

Figure 21A:
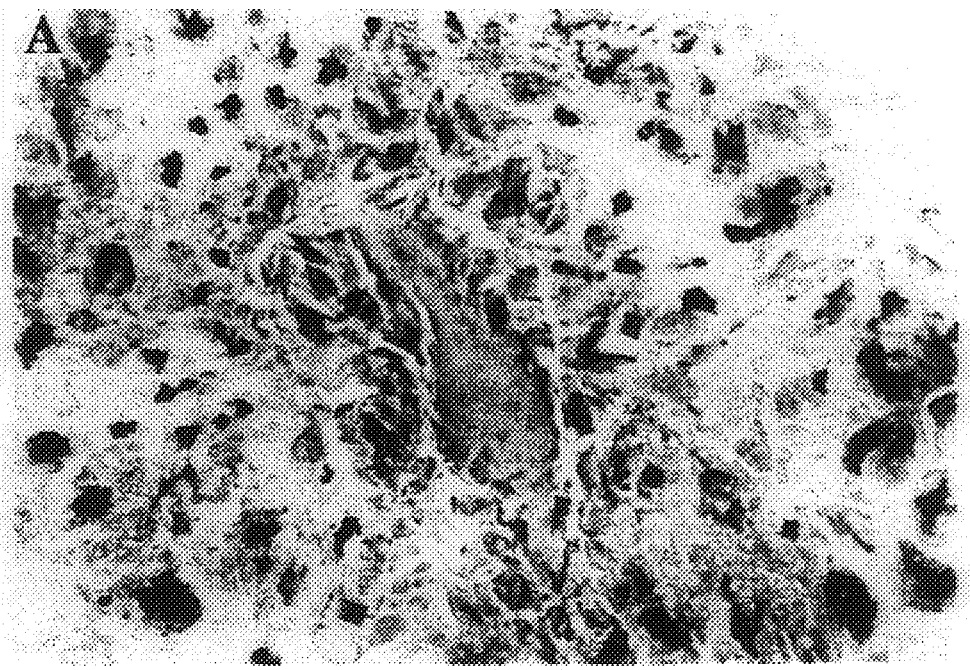
FIGS. 21A and B depict immunohistochemical staining of frozen tissue sections from mouse testis with a monoclonal antibody against TAH protein using avidin-biotinylated-peroxidase detection.
Figure 21B:
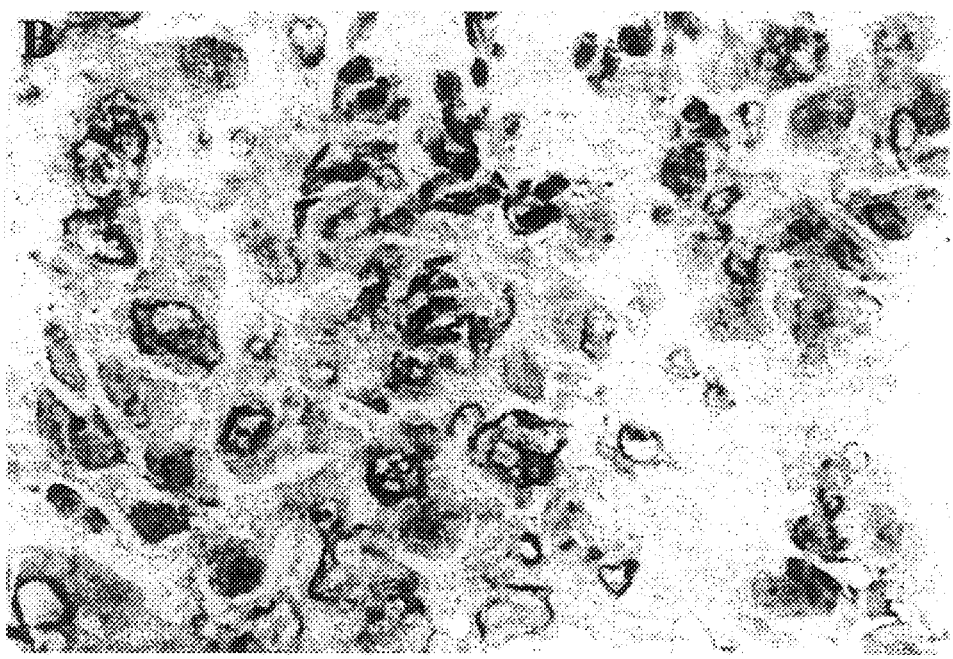

FIG. 21 depicts immunohistochemical staining of frozen tissue sections from mouse testis with a monoclonal antibody against TAH protein using avidin-biotinylated-peroxidase detection. A, showing abundant TAH protein in nuclei of spermatogonia, spermatocytes, but not in that of spermatozoa. B, a negative control.

EXAMPLE 13

Aberrant Expression of TAH in Tumor Tissues and Cancer Cell Lines

Figure 2:
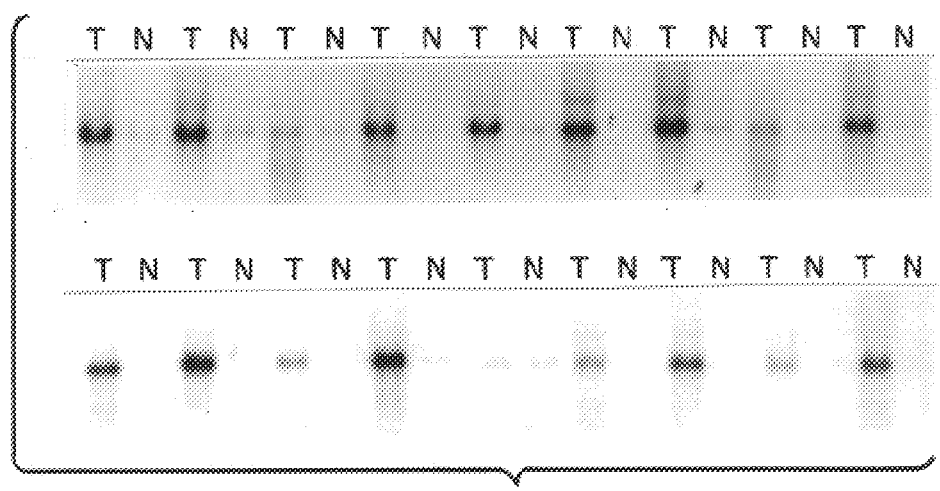
FIG. 2 illustrates differential expression of TAH mRNA in colon tumor tissues confirmed by Northern blot.
Figure 3:
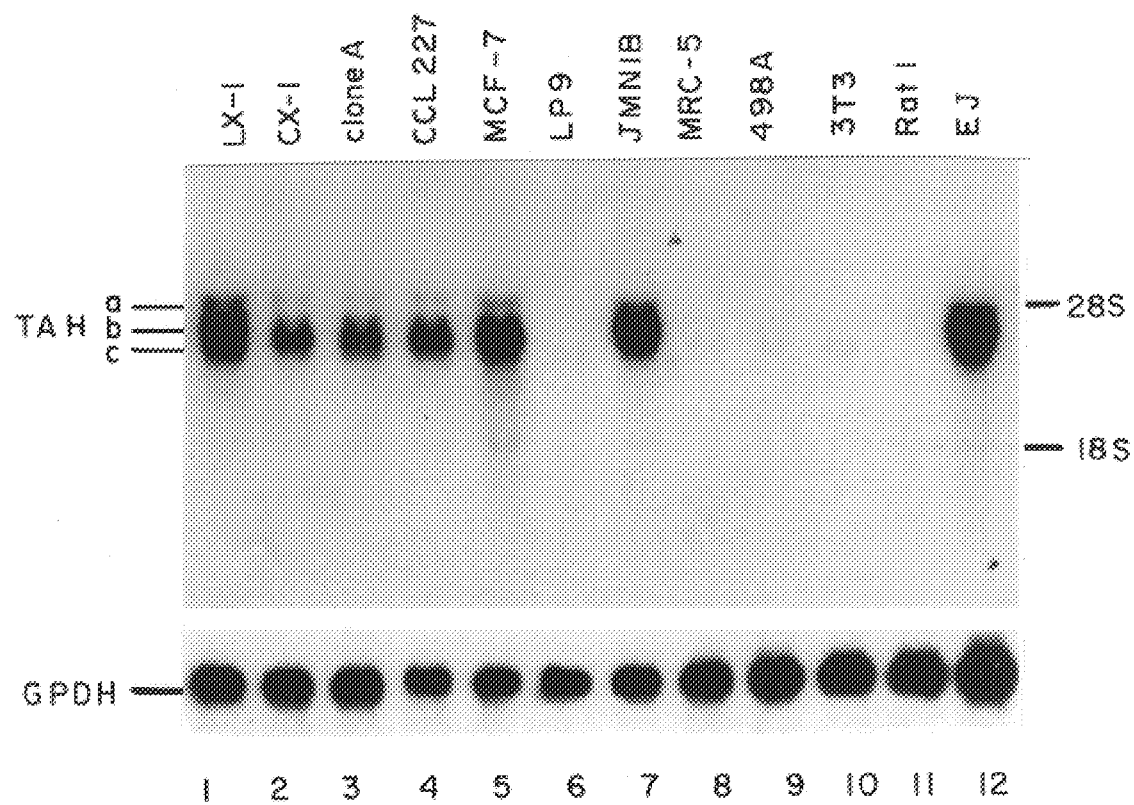
FIG. 3 shows overexpression of TAH mRNA in various cancer cell lines revealed by Northern blot analysis.

Northern blot analysis of TAH mRNA expression in paired human colorectal carcinomas (T) and the adjacent normal colonic epithelia (N) from surgical specimens was performed. Total RNAs from paired samples of colon carcinoma (T) and the adjacent normal colon (N) were probed with a $^{32}$P-labeled TAH cDNA fragment. As shown in FIG. 2, TAH was overexpressed in all surgically removed human colorectal cancers examined, but undetectable in the adjacent normal human colonic tissue.

An extensive screening of more than 100 cell lines including human cancer cell lines, "untransformed", and tumorigenic cell lines of various origins was thus undertaken. The results of this screening revealed that all human cancer cell lines examined and all SV40, polyoma virus, or adenovirus (type 2 and 3) transformed cell lines examined overexpressed TAH, whereas very few normal tissues derived cell lines or cell lines transfected/transformed by a single oncogene such as v-Src, v-Abl, Bcr-Abl, H-Ras, or K-Ras expressed detectable TAH (see, table 1). However, myc transformed cells showed high expression of TAH. This further suggests in myb associated malignant cell TAH is overexpressed.

TABLE 1

Immunofluorescent Stainings of Various Cell Types with TAH mAb (HT-1)

| | TAH Nuclear Stainings |
|---|---|
| Cells Derived from Normal Tissues | |
| Human foreskin fibroblasts | – |
| Human breast epithelial cells | – |
| Human kidney epithelial cells | – |
| Human bladder epithelial cells | – |
| Human mesothelial cells | – |
| Human T lymphocytes | – |
| Human B lymphocytes | – |
| Human macrophages | – |
| Human bone marrow stem cells | – |
| Bovine pericytes | – |
| MDBK, Bovine kidney epithelial cells | – |
| Rabbit bladder epithelial cells | – |
| 3T3, Mouse fibroblasts | – |
| NIH3T3, Mouse fibroblasts | – |
| Rat-1, Rat fibroblasts | – |
| Pt K1, Marsupial kidney epithelial cells | – |
| Pt K2, Marsupial kidney epithelial cells | – |
| NiL-8, Hamster fibroblasts | – |
| Cells Derived from Human Cancers | |
| MIP101, Colorectal carcinoma | +++ |
| DLD-1, Colorectal carcinoma | ++ |
| Clone A, Colorectal carcinoma | +++ |
| Clone D, Colorectal carcinoma | +++ |
| CX-1 Colorectal carcinoma | ++ |
| HT29, Colorectal carcinoma | ++ |
| Moser, Colorectal carcinoma | ++ |
| SK-CO-1, Colorectal carcinoma | ++ |
| RCA, Colorectal carcinoma | + |
| HCT116, Colorectal carcinoma | + |
| CBS, Colorectal carcinoma | + |
| Gly, Colorectal carcinoma | + |
| C. col, Colorectal carcinoma | + |
| COLO 205, Colorectal carcinoma | + |
| HCT116, Colorectal carcinoma | + |
| SW480, Colorectal carcinoma | + |
| LoVo, Colorectal carcinoma | + |
| SW48, Colorectal carcinoma | + |
| MCF7, Breast carcinoma | ++ |
| BT-20, Breast carcinoma | ++ |
| T-47D, Breast carcinoma | ++ |
| MDA-MB-435S. Breast carcinoma | + |
| DU145, Prostate carcinoma | + |
| LNCaP, Prostate carcinoma | + |
| PC-3, Prostate carcinoma | + |
| EJ, Bladder carcinoma | ++ |

TABLE 1-continued

Immunofluorescent Stainings of Various Cell Types with TAH mAb (HT-1)

| | TAH Nuclear Stainings |
|---|---|
| J82, Bladder carcinoma | ++ |
| RT4, Bladder carcinoma | ++ |
| RT112, Bladder carcinoma | + |
| A549, Lung carcinoma | ++ |
| LX-1, Lung carcinoma | + |
| SW10, Lung carcinoma | + |
| HUT-23, Lung carcinoma | + |
| HUT-125, Lung carcinoma | + |
| HeLa, Cervical carcinoma | +++ |
| CaSki, Cervical carcinoma | ++ |
| C-33A, Cervical carcinoma | + |
| Saos-2, Osteosarcoma | + |
| HOS, Osteosarcoma | + |
| 143B, Osteosarcoma | + |
| U-2 OS, Osteosarcoma | + |
| OVCAR-3, Ovarian carcinoma | + |
| SK-OV-3, Ovarian carcinoma | + |
| A431, Vulva carcinoma | ++ |
| A498. Renal carcinoma | ++ |
| CRL1420, Pancreatic carcinoma | ++ |
| JMN-1B, Mesothelioma | ++ |
| SW-13, Adrenocortex carcinoma | ++ |
| LOX, Melanoma | + |
| HepG2, Hepatoma | + |
| HuTu80, Duodenum carcinoma | + |
| HEC-1-A, Endometrial carcinoma | + |
| G402, Renal leiomyoblastoma | + |
| RL, Non-Hodgkin B-cell lymphoma | + |
| K562, Leukemia | |
| Virally-Transformed Cells | |
| SV80, SV40-Human fibroblasts | + |
| THA, SV40-Hamster fibroblasts | + |
| SV3T3 | ++ |
| F18, Adenovirus (type 2)-Rat fibroblasts | ++ |
| F4, Adenovirus (type 2)-Rat fibroblasts | ++ |
| T2C4, Adenovirus (type 2)-Rat fibroblasts | ++ |
| AnAn, RSV-Rat fibroblasts | – |
| Tumorigenic Rodent Cells | |
| HaK, Hamster kidney fibroblasts | ++ |
| MB III, Mouse lymphosarcoma | ++ |
| LLC-WRC 256, Rat Walker carcinoma | + |
| PC-12, Rat pheochromocytoma | + |
| Oncogene-Transformed Cells | |
| v-Src NIH3T3 | – |
| H-Ras NIH3T3 | – |
| K-Ras NIH3T3 | – |
| v-Sis NIH3T3 | – |
| v-Abl 3T3 | – |
| c-Myc 3T3 | +++ |

Northern blot analysis of TAH mRNA expression in various cell lines was performed. Total RNAs was isolated from cancer cell lines (FIGS. 3, 1–5, 7, 12) or normal cell lines (6, 8–11) and blotted with a $^{32}$P-labeled TAH cDNA (top panel) or with a $^{32}$P-labeled G3PDH cDNA (bottom panel). Total RNAs isolated from various cancer cell lines (1–5, 7, 12) or normal cell lines (6, 8–11) were probed with a $^{32}$P-labeled cDNA encoding for G3PDH (bottom panel). Three transcripts (a, b, c) of TAH in cancer cell lines were detected. The major transcript of TAH is about 3.1 kb, other transcripts are about 3.4 kb and 4.0 kb.

As illustrated in FIG. 14, immunofluorescent stainings were used to demonstrate localization of TAH in the nucleus of a number of cell lines: Clone A (human colon carcinoma); MIP101 (human colon carcinoma); and MRC-5 and 3T3 (normal human and mouse fibroblast).

Figure 24A:
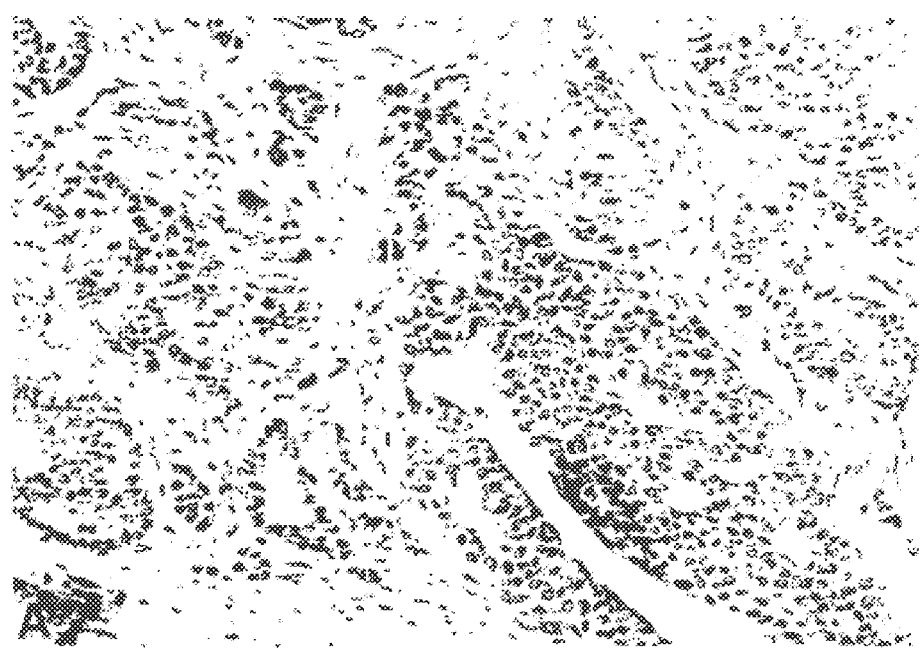
FIGS. 24A and B are immunohistochemical stainings of breast cancer tissue sections with a monoclonal antibody against TAH protein using avidin-biotinylated-peroxidase detection.
Figure 24B:
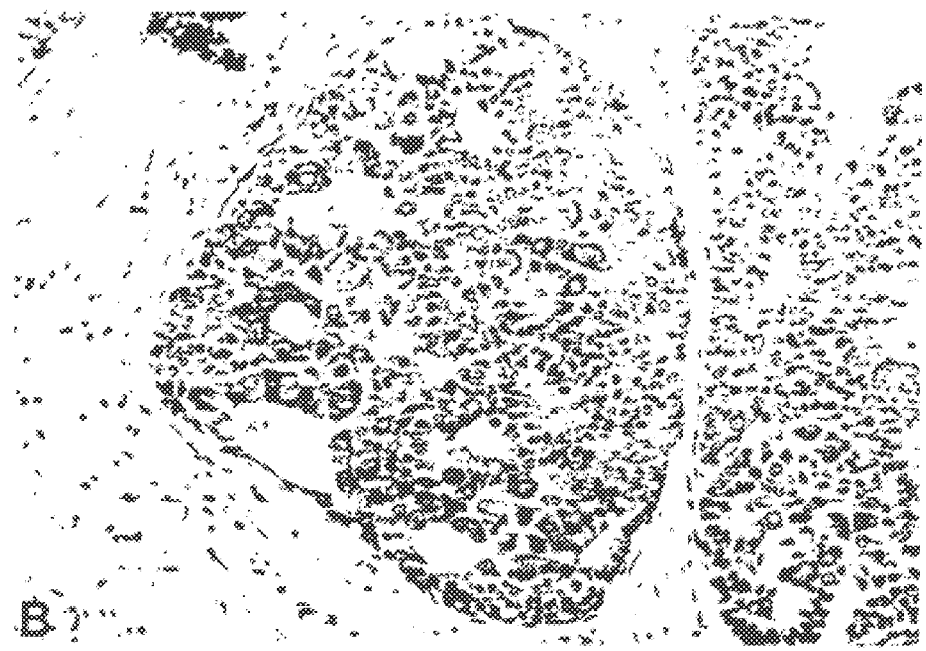

FIG. 24 is an immunohistochemical staining of breast cancer tissue sections with a monoclonal antibody against TAH protein using avidin-biotinylated-peroxidase detection. TAH protein was detected both in invasive ductal breast carcinoma (A) and intra-ductal breast carcinoma (B).

The data presented herein shows that TAH plays a role in UV-induced DNA damage and repair via its helicase activity. Both are rapidly induced by UV irradiation and both confer increased UV resistance. Both proteins require accessory component(s) for efficient ATP-dependent helicase activity. And, both have a similar donut shape as visualized by electron microscopy.

Human TAH complements partially the ruvB-mutants of *E. coli*. Thus, TAH appears to serve a function in human cells analogous to that of RuvB in *E. coli*, i.e. DNA recombinational repair. Recombinational repair system in human cells is relatively unknown. TAH can be used to identify other components in this supramolecular assembly, such as RuvA and RuvC equivalents, through the use TAH-GST beads, crosslinking, and co-immunoprecipitation.

Among all normal tissues examined, only the testis expresses a high level of TAH. Although not wishing to be bound by theory we believe this is because testis, being the organ producing billions of sperm rapidly, needs to use all available DNA repair systems to assure sperm DNA free from any mutations. Moreover, recent studies in yeast demonstrated that homologous pairings in meiotic recombinations are preceded by double-stranded breaks (DSB) at or near the recombination hot spots. Normal crossover during meiosis may use the same molecular machinery employed by DNA recombinational repair. Accordingly, TAH may not only be involved in recombinational repair, but also be an essential component of meiotic crossover.

Thus, TAH can serve a RuvB-equivalent role in humans. Thus, the observation that RuvB, in conjunction with RuvA, RuvC, RecA and other components can promote branch migration of Holliday junctions and its resolution demonstrates that TAH may be involved in recombinational repair in human cells.

TAH, being almost twice larger than RuvB is different and should possess other binding activities not present in RuvB. The additional binding activities might be needed to help the TAH complex find the damaged DNA in mammalian nuclei where DNA sequences are a billion times more abundant than in *E. coli*. In the relatively simple environment of *E. coli*, RuvABC complex might find their targets readily. In the much larger context of mammalian nuclei, TAH complex may require still more accessory proteins to find the damaged DNA in the sea of overwhelmingly undamaged DNA.

One putative accessory protein in the TAH complex is apparently p53. This is because p53 is involved in DNA repair: i) p53 expression is stabilized by UV irradiation; ii) p53 recognizes damaged DNA and binds DNA ends; iii) p53 regulates the expression of excision repair gene GADD45; and iv) p53 is a gatekeeper somehow involved in assuring the replication of "good" but not damaged DNA. Since both w.t. and mutant p53 bind TAH, it is expected that TAH complex are normally under the regulation of w.t. p53, whereas mutant p53 fails to perform this function. TAH can be aided by w.t. p53, but not mutant p53, to find the damaged DNA. In addition, recombinational repair system may have the potential to go haywire and requires a negative regulator such as w.t. p53 to control its function.

Indeed, w.t. p53 has previously been shown to have anti-helicase activity, and, in our assays, TAH's helicase activity is neutralized by w.t. p53 but not mutant p53. During the recovery from UV irradiation, p53 expression did not increase until at least 10 hr after the appearance of TAH. It is consistent with the notion that once TAH completes recombinational repair, it's helicase activity may need to be turned off by w.t. p53. In cancer cells harboring p53 mutation, this negative regulation may thus, not be in place. TAH, unchecked by w.t. p53, might then interact with other nuclear components to engage in faulty or unnecessary repair. If such an unguided repair is a chronic and persistent one, the consequence might be an increase in the rate of mutations. In such context, one might imagine that in testis, although TAH is abundantly expressed, it might be closely regulated by anti-helicase such as p53. Such unregulated helicase has a potential to behave like SV40 T-antigen and contribute to the transformed phenotypes. In such context, one might imagine that in testis, although TAH is abundantly expressed, it might be closely regulated by anti-helicase such as p53.

In cells where there is no p53 mutation, the sequestration of p53 by SV40 T-antigen or E1B, or increased p53 degradation by binding to E6, may create a p53-deficient TAH complex, instead of a mutant p53-TAH complex. If, in these cells, some aberrantly expressed products including transcription factors or other DNA-binding proteins interact with the p53-deficient TAH complex, it may result in a misguided TAH complex capable of illegitimate actions that could further enhance the transformed phenotypes.

While the TAH complex might be involved in DNA repair, it may also influence transcription. The similarities between TAH and SV40 T-antigen, which is known to affect the transcription profoundly, suggest such a possibility. Both TAH and SV40 T-antigen have helicase activity, both bind p53, and both form donut shape. Although TAH does not bind undamaged DNA efficiently (unpublished results), this deficiency might make TAH even more unpredictable in gene regulation since it could potentially interact with a host of transcription factors recognizing different DNA sequences. When the complex binds to a specific promoter, the DNA unwinding activity of TAH could help activate these genes. TAH may therefore be more promiscuous than T-antigen in altering gene expression. It is also possible for a DNA-binding protein that is not normally a transcription factor, to become one, after association with a helicase like TAH.

An aberrant p53 state can be induced by mutation, sequestration or degradation. It then induces a host of abnormalities that culminate in unregulated replication of error-containing DNA. Conceivably, TAH expression alone may lead to similar effects by its potential p53-sequestering activity. Since tumor cells harboring mutant p53, T-antigen, E1B, or E6, express high levels of TAH, the aberrant state of p53 in these cells might be enhanced by TAH, which may sequester still more p53. Adenovirus (type 2)-transformed rat fibroblasts such as F18 express a level of TAH comparable to that of E1B (unpublished results). TAH may be able to sequester as much p53 as that attained by E1B in F18 cells. Moreover, certain p53 "weak" mutants might still be able to function partially as a gatekeeper. These cells might be on the brink of, but not fully trapped in, neoplastic transformation. Expression of TAH might push them over the edge to becoming fully transformed. Thus, apart from its repair function, persistent TAH expression could sequester p53 and be part of a critical turning point in the genesis of cancer at which mutations could breed still more mutations.

Some cancer cells such as the Non-Hodgkin B cell lymphomas are known to have originated by escaping from apoptosis. Since these cells also express TAH, it is tempting to link TAH with apoptosis as well. One obvious route is via p53, known to be intimately involved in apoptosis.

Conceivably, for many Non-Hodgkin B cell lymphomas in which no p53 mutations have been noted, the expression of TAH, activated by unknown mechanisms, could deprive cells of wild-type p53 and help them escape from apoptosis. Thus, in cell lineages where apoptosis is part of the normal course of differentiation, the expression of TAH, even in the absence of abnormal p53, may be detrimental to the balance of cellular renewal. If the TAH expression persists, it may allow cellular evolution including bcl-2 or bcl-x activation to proceed and result in successful malignancy. Thus, in cell lineages where apoptosis is part of the normal course of differentiation, the expression of TAH, even in the absence of abnormal p53, may be detrimental.

Although not wishing to be bound by theory when TAH is constitutively expressed in a variety of cells it leads to human malignancy because cancer cells are known to be more susceptible to DSB and other DNA damages. If such events persist constitutive expression of repair systems including recombinational repair may be required. Alternatively, aberrant gene expression is a hallmark of cancer cells. TAH expression may be part of a general breakdown in gene expression program. If testis-specific transcription factors are aberrantly present, TAH expression may ensue. Finally, TAH expression might be a remanent originated from the cellular evolution of cancer. In the course of tumorigenesis driven by multiple genetic changes, TAH might have aided the emergence of clones with selective advantage. Once successful, these clones may not have the mechanism to turn off TAH expression.

Another possible relationship between TAH and apoptosis in some pre-malignant cells might be imagined as follows. p53, sensing the aberrant state of DNA, might have "planned" to induce apoptosis to eradicate such cells, but the induction of TAH for the repair of DNA damage, may inadvertently neutralize p53 actions. Cells are, thus, "rescued" from death. If the event that induces TAH expression persists, then the cells that should otherwise be eradicated might survive.

While not wishing to be bound by theory, it is believed that either TAH gene is normally repressed by w.t. p53, or, when p53 enters an aberrant state, by mutation, sequestration, degradation, overexpression, phosphorylation or hitherto unknown mechanisms, it leads to the derepression of TAH gene. Supporting evidences include: 1) All tumor cell lines with a p53 mutation or deletion express high levels of TAH; 2) Cells transformed by SV40 T-antigen, E1A/E1B or E6/E7 all express unusually high levels of TAH; 3) When t.s. T-antigen-transformed cells are shifted from nonpermissive to permissive temperature, TAH is dramatically induced (unpublished results). In UV-irradiated cells, w.t. p53, although increased late, could still inhibit the induced-TAH's helicase activity. But in cells with p53 in aberrant state, it may not have the necessary anti-helicase to regulate TAH. Thus, in these cells not only is the TAH gene expression derepressed, but also the helicase activity unchecked.]

Numerous genes that are overexpressed in tumors of a particular cell lineage often are also expressed in normal cells of other lineages. Thus, there is no tumor marker that is totally unexpressed in all normal cells. TAH is no exception. However, since it is only expressed at a high level by normal testis, and most of the surgically removed human cancers and cell lines derived from human cancers examined, TAH is a useful tumor marker for human malignancy. For cancer diagnosis and therapy, TAH finds unique applications, particularly in women, where there are no normal tissues expressing high levels of TAH. Moreover, even in men, a TAH-targeted drug increases the rate of sperm DNA mutations because of a loss of a repair enzyme, could also be used along with the use of contraception.

Again, while not wishing to be bound by theory, TAH expression by human cancer cells plays a role in the resilience of human cancers in resisting therapies such as radiation and chemotherapy. If prior to radiation treatment or chemotherapy, cancer cells express repair enzymes that are normally made in response to genotoxic agents, then this expression might pre-dispose these cells to resistance. The intended use of radiation and chemotherapy to kill cells before damaged DNA can be repaired may therefore be compromised. Alternatively, the majority of cells may be killed but some, perhaps TAH overproducers, could repair damaged DNA efficiently enough for an early recovery. The well-known phenomena of the emergence of highly resistant cells after radiation or chemotherapy might originate from such TAH overproducers.

Finally, mutations in TAH itself or its accessory proteins are be of interest to both sporadic and hereditary human cancers. Analogous to what a mutated hMSH2 gene can do to generate point mutations, a mutated TAH complex could perform faulty repair and result in mutations. In addition, the possibility of mutations in both mismatch repair and recombinational repair systems in sporadic human cancers deserves careful investigation. Futile cycles of DNA damage, illegitimate repair, and mutation may be the prelude to the most intriguing, but horrifying, aspect of human cancers, i.e. the genetic instability.

The references cited throughout the specification are incorporated herein by reference.

This invention has been described in detail including the preferred embodiments thereof. However, it will be appreciated that those skilled in the art, upon consideration of this disclosure, may make modifications and improvements thereon without departing from the spirit and scope of the invention as set forth in the claims.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 2652 base pairs
        ( B ) TYPE: nucleic acid (C) STRANDEDNESS: unknown
(D) TOPOLOGY: unknown (ix) FEATURE:
  (A) NAME/KEY: CDS
  (B) LOCATION: 120..2130

(xi) SEQUENCE DESCRIPTION: SEQ ID NO:1:

```
AATTCGGCAC GAGGCTGTCG AAAGTTTTAC TATAATGAAA GATATTTTCA TACTCTCAAA        60

AATATAGAGG AAAGGGGCCA AGATTATAGT ACCAGTCACA ATCTTTTGAT GAGGACGAA        119

ATG  AAT  CAG  GTA  ACA  GAC  TGG  GTT  GAC  CCA  TCA  TTT  GAT  GAT  TTT  CTA      167
Met  Asn  Gln  Val  Thr  Asp  Trp  Val  Asp  Pro  Ser  Phe  Asp  Asp  Phe  Leu
 1                 5                    10                      15

GAG  TGT  AGT  GGC  GTC  TCT  ACT  ATT  ACT  GCC  ACA  TCA  TTA  GGT  GTG  AAT      215
Glu  Cys  Ser  Gly  Val  Ser  Thr  Ile  Thr  Ala  Thr  Ser  Leu  Gly  Val  Asn
               20                         25                      30

AAC  TCA  AGT  CAT  AGA  AGA  AAA  AAT  GGG  CCT  TCT  ACA  TTA  GAA  AGC  AGC      263
Asn  Ser  Ser  His  Arg  Arg  Lys  Asn  Gly  Pro  Ser  Thr  Leu  Glu  Ser  Ser
               35                         40                      45

AGA  TTT  CCA  GCG  AGA  AAA  AGA  GGA  AAT  CTA  TCT  TCC  TTA  GAA  CAG  ATT      311
Arg  Phe  Pro  Ala  Arg  Lys  Arg  Gly  Asn  Leu  Ser  Ser  Leu  Glu  Gln  Ile
      50                   55                          60

TAT  GGT  TTA  GAA  AAT  TCA  AAA  GAA  TAT  CTG  TCT  GAA  AAT  GAA  CCA  TGG      359
Tyr  Gly  Leu  Glu  Asn  Ser  Lys  Glu  Tyr  Leu  Ser  Glu  Asn  Glu  Pro  Trp
 65                    70                         75                       80

GTG  GAT  AAA  TAT  AAA  CCA  GAA  ACT  CAG  CAT  GAA  CTT  GCT  GTG  CAT  AAA      407
Val  Asp  Lys  Tyr  Lys  Pro  Glu  Thr  Gln  His  Glu  Leu  Ala  Val  His  Lys
                    85                         90                      95

AAG  AAA  ATT  GAA  GAA  GTC  GAA  ACC  TGG  TTA  AAA  GCT  CAA  GTT  TTA  GAA      455
Lys  Lys  Ile  Glu  Glu  Val  Glu  Thr  Trp  Leu  Lys  Ala  Gln  Val  Leu  Glu
               100                        105                     110

AGG  CAA  CCA  AAA  CAG  GGT  GGA  TCT  ATT  TTA  TTA  ATA  ACA  GGT  CCT  CCT      503
Arg  Gln  Pro  Lys  Gln  Gly  Gly  Ser  Ile  Leu  Leu  Ile  Thr  Gly  Pro  Pro
      115                       120                       125

GGA  TGT  GGA  AAG  ACA  ACG  ACC  TTA  AAA  ATA  CTA  TCA  AAG  GAG  CAT  GGT      551
Gly  Cys  Gly  Lys  Thr  Thr  Thr  Leu  Lys  Ile  Leu  Ser  Lys  Glu  His  Gly
      130                       135                       140

ATT  CAA  GTA  CAA  GAG  TGG  ATT  AAT  CCA  GTT  TTA  CCA  GAC  TTC  CAA  AAA      599
Ile  Gln  Val  Gln  Glu  Trp  Ile  Asn  Pro  Val  Leu  Pro  Asp  Phe  Gln  Lys
145                        150                       155                    160

GAT  GAT  TTC  AAG  GGG  ATG  TTT  AAT  ACT  GAA  TCA  AGC  TTC  CAT  ATG  TTT      647
Asp  Asp  Phe  Lys  Gly  Met  Phe  Asn  Thr  Glu  Ser  Ser  Phe  His  Met  Phe
                    165                       170                     175

CCC  TAT  CAG  TCT  CAG  ATA  GCA  GTT  TTC  AAA  GAG  TTT  CTA  CTA  AGA  GCG      695
Pro  Tyr  Gln  Ser  Gln  Ile  Ala  Val  Phe  Lys  Glu  Phe  Leu  Leu  Arg  Ala
               180                        185                    190

ACA  AAG  TAT  AAC  AAG  TTA  CAA  ATG  CTT  GGA  GAT  GAT  CTG  AGA  ACT  GAT      743
Thr  Lys  Tyr  Asn  Lys  Leu  Gln  Met  Leu  Gly  Asp  Asp  Leu  Arg  Thr  Asp
               195                        200                    205

AAG  AAG  ATA  ATT  CTG  GTT  GAA  GAT  TTA  CCT  AAC  CAG  TTT  TAT  CGG  GAT      791
Lys  Lys  Ile  Ile  Leu  Val  Glu  Asp  Leu  Pro  Asn  Gln  Phe  Tyr  Arg  Asp
      210                       215                       220

TCT  CAT  ACT  TTA  CAT  GAA  GTT  CTA  AGG  AAG  TAT  GTG  AGG  ATT  GGT  CGA      839
Ser  His  Thr  Leu  His  Glu  Val  Leu  Arg  Lys  Tyr  Val  Arg  Ile  Gly  Arg
225                        230                       235                    240

TGT  CCT  CTT  ATA  TTT  ATA  ATC  TCG  GAC  AGT  CTC  AGT  GGA  GAT  AAT  AAT      887
Cys  Pro  Leu  Ile  Phe  Ile  Ile  Ser  Asp  Ser  Leu  Ser  Gly  Asp  Asn  Asn
               245                        250                    255

CAA  AGG  TTA  TTG  TTT  CCC  AAA  GAA  ATT  CAG  GAA  GAG  TGT  TCT  ATC  TCA      935
Gln  Arg  Leu  Leu  Phe  Pro  Lys  Glu  Ile  Gln  Glu  Glu  Cys  Ser  Ile  Ser
               260                        265                    270
```

| | | | | | | | | | | | | | | | | |
|---|---|---|---|---|---|---|---|---|---|---|---|---|---|---|---|---|
| AAT | ATT | AGT | TTC | AAC | CCT | GTG | GCA | CCA | ACA | ATT | ATG | ATG | AAA | TTT | CTT | 983 |
| Asn | Ile | Ser | Phe | Asn | Pro | Val | Ala | Pro | Thr | Ile | Met | Met | Lys | Phe | Leu | |
| | | 275 | | | 280 | | | | | | | 285 | | | | |
| AAT | CGA | ATA | GTG | ACT | ATA | GAA | GCT | AAC | AAG | AAT | GGA | GGA | AAA | ATT | ACT | 1031 |
| Asn | Arg | Ile | Val | Thr | Ile | Glu | Ala | Asn | Lys | Asn | Gly | Gly | Lys | Ile | Thr | |
| | 290 | | | | | 295 | | | | | 300 | | | | | |
| GTC | CCT | GAC | AAA | ACT | TCT | CTA | GAG | TTG | CTC | TGT | CAG | GGA | TGT | TCT | GGT | 1079 |
| Val | Pro | Asp | Lys | Thr | Ser | Leu | Glu | Leu | Leu | Cys | Gln | Gly | Cys | Ser | Gly | |
| 305 | | | | | 310 | | | | | 315 | | | | | 320 | |
| GAT | ATC | AGA | AGT | GCA | ATA | AAC | AGC | CTC | CAG | TTT | TCT | TCT | TCA | AAA | GGA | 1127 |
| Asp | Ile | Arg | Ser | Ala | Ile | Asn | Ser | Leu | Gln | Phe | Ser | Ser | Ser | Lys | Gly | |
| | | | | 325 | | | | | 330 | | | | | 335 | | |
| GAA | AAC | AAC | TTA | CGG | CCA | AGG | AAA | AAA | GGA | ATG | TCT | TTA | AAA | TCA | GAT | 1175 |
| Glu | Asn | Asn | Leu | Arg | Pro | Arg | Lys | Lys | Gly | Met | Ser | Leu | Lys | Ser | Asp | |
| | | | | 340 | | | | | 345 | | | | | 350 | | |
| GCT | GTG | CTG | TCA | AAA | TCA | AAA | CGA | AGA | AAA | AAA | CCT | GAT | AGG | GTT | TTT | 1223 |
| Ala | Val | Leu | Ser | Lys | Ser | Lys | Arg | Arg | Lys | Lys | Pro | Asp | Arg | Val | Phe | |
| | | 355 | | | | | 360 | | | | | 365 | | | | |
| GAA | AAT | CAA | GAG | GTC | CAA | GCT | ATT | GGT | GGC | AAA | GAT | GTT | TCT | CTG | TTT | 1271 |
| Glu | Asn | Gln | Glu | Val | Gln | Ala | Ile | Gly | Gly | Lys | Asp | Val | Ser | Leu | Phe | |
| | 370 | | | | | 375 | | | | | 380 | | | | | |
| CTC | TTC | AGA | GCT | TTG | GGG | AAA | ATT | CTA | TAT | TGT | AAA | AGA | GCA | TCT | TTA | 1319 |
| Leu | Phe | Arg | Ala | Leu | Gly | Lys | Ile | Leu | Tyr | Cys | Lys | Arg | Ala | Ser | Leu | |
| 385 | | | | | 390 | | | | | 395 | | | | | 400 | |
| ACA | GAA | TTA | GAC | TCA | CCT | CGG | TTG | CCC | TCT | CAT | TTA | TCA | GAA | TAT | GAA | 1367 |
| Thr | Glu | Leu | Asp | Ser | Pro | Arg | Leu | Pro | Ser | His | Leu | Ser | Glu | Tyr | Glu | |
| | | | | 405 | | | | | 410 | | | | | 415 | | |
| CGG | GAT | ACA | TTA | CTT | GTT | GAA | CCT | GAG | GAG | GTA | GTA | GAA | ATG | TCA | CAC | 1415 |
| Arg | Asp | Thr | Leu | Leu | Val | Glu | Pro | Glu | Glu | Val | Val | Glu | Met | Ser | His | |
| | | | 420 | | | | | 425 | | | | | 430 | | | |
| ATG | CCT | GGA | GAC | TTA | TTT | AAT | TTA | TAT | CTT | CAC | CAA | AAC | TAC | ATA | GAT | 1463 |
| Met | Pro | Gly | Asp | Leu | Phe | Asn | Leu | Tyr | Leu | His | Gln | Asn | Tyr | Ile | Asp | |
| | | 435 | | | | | 440 | | | | | 445 | | | | |
| TTC | TTC | ATG | GAA | ATT | GAT | GAT | ATT | GTG | AGA | GCC | AGT | GAA | TTT | CTG | AGT | 1511 |
| Phe | Phe | Met | Glu | Ile | Asp | Asp | Ile | Val | Arg | Ala | Ser | Glu | Phe | Leu | Ser | |
| | 450 | | | | | 455 | | | | | 460 | | | | | |
| TTT | GCA | GAT | ATC | CTC | AGT | GGT | GAC | TGG | AAT | ACA | CGC | TCT | TTA | CTC | AGG | 1559 |
| Phe | Ala | Asp | Ile | Leu | Ser | Gly | Asp | Trp | Asn | Thr | Arg | Ser | Leu | Leu | Arg | |
| 465 | | | | | 470 | | | | | 475 | | | | | 480 | |
| GAA | TAT | AGC | ACA | TCT | ATA | GCT | ACG | AGA | GGT | GTG | ATG | CAT | TCC | AAC | AAA | 1607 |
| Glu | Tyr | Ser | Thr | Ser | Ile | Ala | Thr | Arg | Gly | Val | Met | His | Ser | Asn | Lys | |
| | | | | 485 | | | | | 490 | | | | | 495 | | |
| GCC | CGA | GGA | TAT | GCT | CAT | TGC | CAA | GGA | GGA | GGA | TCA | AGT | TTT | CGA | CCC | 1655 |
| Ala | Arg | Gly | Tyr | Ala | His | Cys | Gln | Gly | Gly | Gly | Ser | Ser | Phe | Arg | Pro | |
| | | | | 500 | | | | | 505 | | | | | 510 | | |
| TTG | CAC | AAA | CCT | CAG | TGG | TTT | CTA | ATA | AAT | AAA | AAG | TAT | CGG | GAA | AAT | 1703 |
| Leu | His | Lys | Pro | Gln | Trp | Phe | Leu | Ile | Asn | Lys | Lys | Tyr | Arg | Glu | Asn | |
| | | 515 | | | | | 520 | | | | | 525 | | | | |
| TGC | CTG | GCA | GCA | AAA | GCA | CTT | TTT | CCT | GAC | TTC | TGC | CTA | CCA | GCT | TTA | 1751 |
| Cys | Leu | Ala | Ala | Lys | Ala | Leu | Phe | Pro | Asp | Phe | Cys | Leu | Pro | Ala | Leu | |
| | 530 | | | | | 535 | | | | | 540 | | | | | |
| TGC | CGC | CAA | ACT | CAG | CTA | TTG | CCA | TAC | CTT | GCT | CTA | CTA | ACC | ATT | CCA | 1799 |
| Cys | Arg | Gln | Thr | Gln | Leu | Leu | Pro | Tyr | Leu | Ala | Leu | Leu | Thr | Ile | Pro | |
| 545 | | | | | 550 | | | | | 555 | | | | | 560 | |
| ATG | AGA | AAT | CAA | GCT | CAG | ATT | TCT | TTT | ATC | CAA | GAT | ATT | GGA | AGG | CTC | 1847 |
| Met | Arg | Asn | Gln | Ala | Gln | Ile | Ser | Phe | Ile | Gln | Asp | Ile | Gly | Arg | Leu | |
| | | | | 565 | | | | | 570 | | | | | 575 | | |
| CCT | CTG | AAG | CGA | CAC | TTT | GGA | AGA | TTG | AAA | ATG | GAA | GCC | CTG | ACT | GAC | 1895 |
| Pro | Leu | Lys | Arg | His | Phe | Gly | Arg | Leu | Lys | Met | Glu | Ala | Leu | Thr | Asp | |
| | | | 580 | | | | | 585 | | | | | 590 | | | |

```
AGG  GAA  CAT  GGA  ATG  ATA  GAC  CCT  GAC  AGC  GGA  GAT  GAA  GCC  CAG  CTT     1943
Arg  Glu  His  Gly  Met  Ile  Asp  Pro  Asp  Ser  Gly  Asp  Glu  Ala  Gln  Leu
          595                      600                     605

AAT  GGA  GGA  CAT  TCT  GCA  GAG  GAA  TCT  CTG  GGT  GAA  CCC  ACT  CAA  GCC     1991
Asn  Gly  Gly  His  Ser  Ala  Glu  Glu  Ser  Leu  Gly  Glu  Pro  Thr  Gln  Ala
          610                      615                     620

ACT  GTG  CCG  GAA  ACC  TGG  TCT  CTT  CCT  TTG  AGT  CAG  AAT  AGT  GCC  AGT     2039
Thr  Val  Pro  Glu  Thr  Trp  Ser  Leu  Pro  Leu  Ser  Gln  Asn  Ser  Ala  Ser
625                      630                     635                      640

GAA  CTG  CCT  GCT  AGC  CAG  CCC  CAG  CCC  TTT  TCA  GCC  CAA  GGA  GAC  ATG     2087
Glu  Leu  Pro  Ala  Ser  Gln  Pro  Gln  Pro  Phe  Ser  Ala  Gln  Gly  Asp  Met
               645                      650                     655

GAA  GAA  AAC  ATA  ATA  ATA  GAA  GAC  TAC  GAG  AGT  GAT  GGG  ACA  T            2130
Glu  Glu  Asn  Ile  Ile  Ile  Glu  Asp  Tyr  Glu  Ser  Asp  Gly  Thr
               660                      665                     670

AGAAGCCAGC  CTGCTAATCA  GATTGCTACT  TCACAGCTTC  ATTTTGTTT  CATTCAGTGG              2190

TACTTCAGCA  GAGTTAATAT  GCTTTTCTGA  TGAATTACAC  AACAGTTTGT  TAATTCTTCA              2250

TTCTTGTAGT  ATTTCATCAC  AAGAAACCTA  CTCTTCTGTC  ATCTTGAAGT  AAATAGAAGA              2310

TCAAGCCTTC  AAATCTCTTA  ATTTTTTCGG  TATTTATTAA  ATCTGTGAGT  GGTTTAAGGA              2370

GCGGTCAGTG  TGTATAAAGT  GTGTTTGAAC  ATTATGCCAA  ATATCAAGAT  GTGAAGGACT              2430

AATTCAGGAT  GCAAAAACGT  TATTGGGGGG  TTGTAAATAT  CAACTATTCA  ACAGTTTAGG              2490

ATGCAATTAC  GAGTGTAAAC  TGTGTGCCTT  ATTACACTT   TATTGTCTCC  CGCTTCTCAG              2550

ATAGTTTTGA  TGTGTTGTAC  AGTGGAATAT  CTTAGATACT  TTTTGGAAAG  TATTTACATA              2610

AGTTATATCA  CAATTAAAAT  GTTGAATTTC  TCGTGCCGAA  TT                                  2652
```

( 2 ) INFORMATION FOR SEQ ID NO:2:

( i ) SEQUENCE CHARACTERISTICS:
    ( A ) LENGTH: 670 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

```
Met  Asn  Gln  Val  Thr  Asp  Trp  Val  Asp  Pro  Ser  Phe  Asp  Asp  Phe  Leu
 1              5                    10                      15

Glu  Cys  Ser  Gly  Val  Ser  Thr  Ile  Thr  Ala  Thr  Ser  Leu  Gly  Val  Asn
               20                      25                      30

Asn  Ser  Ser  His  Arg  Arg  Lys  Asn  Gly  Pro  Ser  Thr  Leu  Glu  Ser  Ser
               35                      40                      45

Arg  Phe  Pro  Ala  Arg  Lys  Arg  Gly  Asn  Leu  Ser  Ser  Leu  Glu  Gln  Ile
          50                      55                      60

Tyr  Gly  Leu  Glu  Asn  Ser  Lys  Glu  Tyr  Leu  Ser  Glu  Asn  Glu  Pro  Trp
 65                      70                      75                      80

Val  Asp  Lys  Tyr  Lys  Pro  Glu  Thr  Gln  His  Glu  Leu  Ala  Val  His  Lys
               85                      90                      95

Lys  Lys  Ile  Glu  Glu  Val  Glu  Thr  Trp  Leu  Lys  Ala  Gln  Val  Leu  Glu
               100                     105                     110

Arg  Gln  Pro  Lys  Gln  Gly  Gly  Ser  Ile  Leu  Leu  Ile  Thr  Gly  Pro  Pro
          115                     120                     125

Gly  Cys  Gly  Lys  Thr  Thr  Thr  Leu  Lys  Ile  Leu  Ser  Lys  Glu  His  Gly
          130                     135                     140

Ile  Gln  Val  Gln  Glu  Trp  Ile  Asn  Pro  Val  Leu  Pro  Asp  Phe  Gln  Lys
 145                     150                     155                     160
```

```
Asp Asp Phe Lys Gly Met Phe Asn Thr Glu Ser Ser Phe His Met Phe
            165                 170                 175
Pro Tyr Gln Ser Gln Ile Ala Val Phe Lys Glu Phe Leu Leu Arg Ala
            180                 185                 190
Thr Lys Tyr Asn Lys Leu Gln Met Leu Gly Asp Asp Leu Arg Thr Asp
            195                 200                 205
Lys Lys Ile Ile Leu Val Glu Asp Leu Pro Asn Gln Phe Tyr Arg Asp
    210                 215                 220
Ser His Thr Leu His Glu Val Leu Arg Lys Tyr Val Arg Ile Gly Arg
225                 230                 235                 240
Cys Pro Leu Ile Phe Ile Ile Ser Asp Ser Leu Ser Gly Asp Asn Asn
                245                 250                 255
Gln Arg Leu Leu Phe Pro Lys Glu Ile Gln Glu Glu Cys Ser Ile Ser
            260                 265                 270
Asn Ile Ser Phe Asn Pro Val Ala Pro Thr Ile Met Met Lys Phe Leu
        275                 280                 285
Asn Arg Ile Val Thr Ile Glu Ala Asn Lys Asn Gly Gly Lys Ile Thr
        290                 295                 300
Val Pro Asp Lys Thr Ser Leu Glu Leu Leu Cys Gln Gly Cys Ser Gly
305                 310                 315                 320
Asp Ile Arg Ser Ala Ile Asn Ser Leu Gln Phe Ser Ser Ser Lys Gly
                325                 330                 335
Glu Asn Asn Leu Arg Pro Arg Lys Lys Gly Met Ser Leu Lys Ser Asp
            340                 345                 350
Ala Val Leu Ser Lys Ser Lys Arg Arg Lys Lys Pro Asp Arg Val Phe
            355                 360                 365
Glu Asn Gln Glu Val Gln Ala Ile Gly Gly Lys Asp Val Ser Leu Phe
        370                 375                 380
Leu Phe Arg Ala Leu Gly Lys Ile Leu Tyr Cys Lys Arg Ala Ser Leu
385                 390                 395                 400
Thr Glu Leu Asp Ser Pro Arg Leu Pro Ser His Leu Ser Glu Tyr Glu
                405                 410                 415
Arg Asp Thr Leu Leu Val Glu Pro Glu Val Val Glu Met Ser His
            420                 425                 430
Met Pro Gly Asp Leu Phe Asn Leu Tyr Leu His Gln Asn Tyr Ile Asp
            435                 440                 445
Phe Phe Met Glu Ile Asp Asp Ile Val Arg Ala Ser Glu Phe Leu Ser
        450                 455                 460
Phe Ala Asp Ile Leu Ser Gly Asp Trp Asn Thr Arg Ser Leu Leu Arg
465                 470                 475                 480
Glu Tyr Ser Thr Ser Ile Ala Thr Arg Gly Val Met His Ser Asn Lys
                485                 490                 495
Ala Arg Gly Tyr Ala His Cys Gln Gly Gly Gly Ser Ser Phe Arg Pro
            500                 505                 510
Leu His Lys Pro Gln Trp Phe Leu Ile Asn Lys Lys Tyr Arg Glu Asn
        515                 520                 525
Cys Leu Ala Ala Lys Ala Leu Phe Pro Asp Phe Cys Leu Pro Ala Leu
        530                 535                 540
Cys Arg Gln Thr Gln Leu Leu Pro Tyr Leu Ala Leu Leu Thr Ile Pro
545                 550                 555                 560
Met Arg Asn Gln Ala Gln Ile Ser Phe Ile Gln Asp Ile Gly Arg Leu
                565                 570                 575
Pro Leu Lys Arg His Phe Gly Arg Leu Lys Met Glu Ala Leu Thr Asp
```

-continued

|   |   |   |   |   |   |   | 580 |   |   |   | 585 |   |   |   | 590 |   |   |   |
|---|---|---|---|---|---|---|---|---|---|---|---|---|---|---|---|---|---|---|
| Arg | Glu | His<br>595 | Gly | Met | Ile | Asp | Pro<br>600 | Asp | Ser | Gly | Asp | Glu<br>605 | Ala | Gln | Leu |
| Asn | Gly<br>610 | Gly | His | Ser | Ala | Glu | Glu<br>615 | Ser | Leu | Gly | Glu | Pro<br>620 | Thr | Gln | Ala |
| Thr<br>625 | Val | Pro | Glu | Thr | Trp<br>630 | Ser | Leu | Pro | Leu | Ser<br>635 | Gln | Asn | Ser | Ala | Ser<br>640 |
| Glu | Leu | Pro | Ala | Ser<br>645 | Gln | Pro | Gln | Pro | Phe<br>650 | Ser | Ala | Gln | Gly | Asp<br>655 | Met |
| Glu | Glu | Asn | Ile<br>660 | Ile | Ile | Glu | Asp | Tyr<br>665 | Glu | Ser | Asp | Gly | Thr<br>670 |   |   |

What is claimed is:

1. An isolated nucleotide sequence encoding a human TAH protein having an amino acid sequence as set forth in SEQ ID:No.2, or an allelic variation thereof, and having helicase and p53 binding activity.

2. The isolated nucleotide sequence of claim 1 wherein the protein has the amino acid sequence of SEQ ID:No.2.

3. An isolated nucleotide sequence having the sequence as set forth in SEQ ID NO:1.

4. An isolated nucleotide sequence having the complementary sequence of SEQ ID NO: 1.

5. A vector containing the nucleotide sequence of claim 3 or 4.

6. A host cell transformed with the vector of claim 5.

7. The isolated nucleotide sequence of claims 3, 4, 1 or 2 bound to a cytotoxic moiety.

8. A vector containing the nucleotide sequence of claim 1.

9. A host cell transformed by the vector of claim 8.

10. A method for enhancing cellular resistance to mutagenesis as a result of U.V. irradiation comprising transfecting a host cell with the nucleotide sequence of claim 1.

11. An isolated nucleotide sequence having nucleotides 495–518, 1140–1154, 1191–1205 or 1306–1332 of SEQ ID:No.1.

12. An isolated nucleotide sequence encoding amino acids 126–133, 341–345, 359–363 or 396–404 of SEQ ID:No.2.

13. A host cell transformed with an isolated nucleotide sequence of claims 11 or 12.

\* \* \* \* \*

UNITED STATES PATENT AND TRADEMARK OFFICE
CERTIFICATE OF CORRECTION

PATENT NO. : 5,843,737
DATED : December 1, 1998
INVENTOR(S) : Lan Bo Chen, Shideng Bao It is certified that error appears in the above-identified patent and that said Letters Patent is hereby corrected as shown below:

Col. 1, before line 4, insert -- -The above invention was made, in part, with support from NIH Grant No. CA51946 and the United States Government has certain rights thereto.- -

Signed and Sealed this

Twenty-seventh Day of July, 1999

Attest:

Q. TODD DICKINSON

Attesting Officer
Acting Commissioner of Patents and Trademarks